United States Patent
Tsuda et al.

(10) Patent No.: US 9,005,529 B2
(45) Date of Patent: Apr. 14, 2015

(54) ION GENERATING APPARATUS AND AIR PURIFYING APPARATUS

(75) Inventors: Tsutomu Tsuda, Osaka (JP); Ichiro Yoshimura, Osaka (JP); Hiromu Nishida, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 339 days.

(21) Appl. No.: 13/061,099

(22) PCT Filed: Mar. 17, 2009

(86) PCT No.: PCT/JP2009/055141
§ 371 (c)(1),
(2), (4) Date: Feb. 25, 2011

(87) PCT Pub. No.: WO2010/023980
PCT Pub. Date: Mar. 4, 2010

(65) Prior Publication Data
US 2011/0150710 A1  Jun. 23, 2011

(30) Foreign Application Priority Data

Aug. 28, 2008 (JP) ................. 2008-220324
Aug. 28, 2008 (JP) ................. 2008-220327
Aug. 28, 2008 (JP) ................. 2008-220329

(51) Int. Cl.
*A61L 9/22* (2006.01)
*B03C 3/38* (2006.01)
*F24F 3/16* (2006.01)

(52) U.S. Cl.
CPC .............. *A61L 9/22* (2013.01); *A61L 2209/134* (2013.01); *B03C 3/383* (2013.01); *F24F 2003/1635* (2013.01); *F24F 2003/1682* (2013.01)

(58) Field of Classification Search
CPC .............. A61L 2/00; A61L 2/02; A61L 2/14; A61L 9/00; A61L 9/16; A61L 9/22; A61L 2209/00; A61L 2209/10; A61L 2209/11; A61L 2209/13; H01T 23/00
USPC ............... 422/120–121, 123–124; 250/423 R
See application file for complete search history.

(56) References Cited

U.S. PATENT DOCUMENTS 4,951,172 A   8/1990  Steinman et al.
6,668,563 B2  12/2003 Mirowsky et al.
(Continued)

FOREIGN PATENT DOCUMENTS

EP   1 671 659 A1   6/2006
EP   2 413 443 A1   5/2011
(Continued)

OTHER PUBLICATIONS

Machine Translation of JP2007-012422, provided by JIPO, retreived Apr. 15, 2013.*

(Continued)

*Primary Examiner* — Sean E Conley
(74) *Attorney, Agent, or Firm* — Birch, Stewart, Kolasch & Birch, LLP

(57) ABSTRACT

A housing having a suction port and a discharge port, an impeller 21 and a casing 22 that houses the impeller 21, an air blower 2 housed in the housing, a filter that lets through the air suctioned from the suction port by the air blower 2, and two ion generating sections that generate positive and negative ions are provided. The ion generating section is arranged on a circular-arc guide wall 2a in the casing 22. The positive and negative ions generated by the ion generating section are efficiently included in the air passing through as laminar flow along the circular-arc guide wall 22a.

6 Claims, 20 Drawing Sheets

(56) References Cited

U.S. PATENT DOCUMENTS

| | | |
|---|---|---|
| 2002/0122751 A1 | 9/2002 | Sinaiko et al. |
| 2002/0134664 A1* | 9/2002 | Taylor et al. .................. 204/164 |
| 2009/0042502 A1 | 2/2009 | Kim et al. |

FOREIGN PATENT DOCUMENTS

| | | |
|---|---|---|
| JP | 2-152561 A | 6/1990 |
| JP | 7-44079 B2 | 5/1995 |
| JP | 2001-110590 | 4/2001 |
| JP | 2002-90058 A | 3/2002 |
| JP | 2002-257408 A | 9/2002 |
| JP | 2003-90571 A | 3/2003 |
| JP | 2004-329639 A | 11/2004 |
| JP | 2004-347264 A | 12/2004 |
| JP | 2005-76906 A | 3/2005 |
| JP | 2005-243288 A | 9/2005 |
| JP | 2005-328904 A | 12/2005 |
| JP | 2005-337610 A | 12/2005 |
| JP | 2006-027922 A | 2/2006 |
| JP | 2006-46732 A | 2/2006 |
| JP | 2 325 961 A1 | 6/2006 |
| JP | 2006-198029 A | 8/2006 |
| JP | 3859762 B2 | 9/2006 |
| JP | 2007-12422 A | 1/2007 |
| JP | 2007-21099 A | 2/2007 |
| JP | 2007-29497 A | 2/2007 |
| JP | 2007-40648 A | 2/2007 |
| JP | 2007-114177 A | 5/2007 |
| JP | 2007-157482 A | 6/2007 |
| JP | 2007-205712 A | 8/2007 |
| JP | 2007-222303 A | 9/2007 |
| JP | 2007-258073 A | 10/2007 |
| JP | 2007-322090 A | 12/2007 |
| JP | 2008-14527 A | 1/2008 |
| JP | 2008-59795 A | 3/2008 |
| JP | 2008-123917 A | 5/2008 |

OTHER PUBLICATIONS

European Search Report issued in European Application No. 10764319.9 on Oct. 26, 2012.

Korean Office Action issued in Korean Patent Application No. 10-2011-7027187 on Apr. 29, 2013.

U.S. Office Action issued in U.S. Appl. No. 13/264,434 on Mar. 20, 2013.

Final Office Action of U.S. Appl. No. 13/264,434 dated Oct. 25, 2013.

U.S. Advisory Action mailed Feb. 28, 2014 for U.S. Appl. No. 13/264,434.

U.S. Office Action, dated Apr. 8, 2014, issued in U.S. Appl. No. 13/264,434.

Sep. 9, 2014 Notice of Allowance issued in related U.S. Appl. No. 13/264,434.

* cited by examiner

● : MEASUREMENT POINT
(2.5M IN HEIGHT)

F I G. 1 3

| NUMBER OF ION GENERATORS | ON/OFF TIME | POSITIVE ION (NUMBER OF IONS/cm³) | NEGATIVE ION (NUMBER OF IONS/cm³) | ION BALANCE (-/+) | RATIO OF ION CONCENTRATION (VS. "CONSTANTLY ON")(%) | | |
|---|---|---|---|---|---|---|---|
| | | | | | POSITIVE ION | NEGATIVE ION | AVERAGE VALUE |
| 1 | CONSTANTLY ON | 14,000 | 14,000 | 1.00 | 100.0 | 100.0 | 100.0 |
| 1 | ON/OFF FOR 0.5 SEC | 12,000 | 12,000 | 1.00 | 85.7 | 85.7 | 85.7 |
| 1 | ON/OFF FOR 1 SEC | 12,000 | 12,000 | 1.00 | 85.7 | 85.7 | 85.7 |
| 1 | ON/OFF FOR 2 SEC | 11,000 | 11,000 | 1.00 | 78.6 | 78.6 | 78.6 |
| 1 | ON/OFF FOR 5 SEC | 10,000 | 11,000 | 1.10 | 71.4 | 78.6 | 75.0 |

FIG. 15

| NUMBER OF ION GENERATORS | ON/OFF TIME | POSITIVE ION (NUMBER OF IONS/cm$^3$) | NEGATIVE ION (NUMBER OF IONS/cm$^3$) | ION BALANCE (−/+) | RATIO OF ION CONCENTRATION (VS. "2 GENERATORS CONSTANTLY ON")(%) | | |
|---|---|---|---|---|---|---|---|
| | | | | | POSITIVE ION | NEGATIVE ION | AVERAGE VALUE |
| 1 | CONSTANTLY ON | 24,129 | 23,781 | 0.99 | 90.3 | 88.4 | 89.4 |
| 2 | CONSTANTLY ON | 26,711 | 26,911 | 1.01 | 100.0 | 100.0 | 100.0 |
| 2 | ON/OFF FOR 0.5 SEC | 24,188 | 24,735 | 1.02 | 90.6 | 91.9 | 91.2 |
| 2 | ON/OFF FOR 1 SEC | 24,876 | 24,537 | 0.99 | 93.1 | 91.2 | 92.2 |
| 2 | ON/OFF FOR 2 SEC | 24,607 | 23,907 | 0.97 | 92.1 | 88.8 | 90.5 |
| 2 | ON/OFF FOR 5 SEC | 25,022 | 23,939 | 0.96 | 93.7 | 89.0 | 91.3 |

ION GENERATING APPARATUS AND AIR PURIFYING APPARATUS

1. FIELD OF THE INVENTION

The present invention relates to an ion generating apparatus and an air purifying apparatus that discharge ions generated by an ion generating section into a room together with the air suctioned by an air blower to purify the air in the room.

2. DESCRIPTION OF THE RELATED ART

Air in a residential room is contaminated with dust of mites, allergic substances such as pollens, floating fungus, virus, foul odors and the like. Moreover, such contaminants tend to remain in a room due to recent improvement in house airtightness, requiring active air ventilation. In a room located in an area with serious air pollution or in a room where a person having an allergy to pollens lives or works, however, an air purifying apparatus is used, since ventilation by opening a window may not be possible as desired.

The air purifying apparatus includes: an air blower housed in a housing having a suction port on a back surface thereof and a discharge port at an upper part thereof; a filter that lets through the air suctioned from the suction port by the air blower; and an ion generating section that generates ions. The air purifying apparatus is further configured to discharge the ions generated by the ion generating section from the discharge port into a room together with the air suctioned by the air blower, so that the ions decompose contaminants in the room and purifies the room air (see Patent Document 1, for example).

The ion generating section has a positive electrode and a negative electrode that are arranged separately from each other in a juxtaposed manner. A potential is applied between the positive electrode and the negative electrode so that positive ions are discharged from the positive electrode while negative ions are discharged from the negative electrode. The discharged positive ions and negative ions are included in the air suctioned by the air blower and discharged from the discharge port together with the air.

In recent years, a technique of purifying the air in a residential room by discharging positive (plus) and/or negative (minus) ions into the residential room has widely been used. For example, in an air purifier, an ion generator that generates positive and negative ions is arranged in the middle of an inside air-flowing path to discharge the generated ions to an external space together with the air in the air-flowing path.

The ions discharged to the outside together with the air inactivate floating particles in a residential room and kill floating bacteria, purifying the air in the entire residential room.

A general ion generator applies a high and alternating driving voltage between a needle electrode and an opposite electrode or between a discharge electrode and a dielectric electrode, to cause corona discharge to generate positive and negative ions. It is not easy to recognize whether or not ions are actually generated, since the generated ions are colorless and odorless.

To address the above, Patent Document 2 discloses a technique of detecting presence/absence of generated ions. Patent Document 3 discloses a technique of detecting the amount of generated ions and optimally controlling the amount of generated ions.

In recent years, a technique of purifying air in a residential space by charging water molecules in the air with positive (plus) and/or negative (minus) ions has widely been used. For example, in an air purifier, an ion generating apparatus that generates positive and negative ions is arranged in the middle of the inside air-flowing path to discharge the generated ions to the outside space together with the air.

The ions charging the water molecules in the clean air inactivate floating particles and kill floating bacteria in a residential space, purifying the air in the entire residential space.

A standard ion generating apparatus causes corona discharge to generate positive and negative ions by applying a high and alternating driving voltage between a needle electrode and an opposite electrode or between a discharge electrode and an opposite electrode. Moreover, an ion generator in which the electrodes described above and a circuit generating a driving voltage are integrated has been disclosed (see Patent Document 4, for example), while an air purifier with a built-in ion generator has come into practical use.

One ion generator may, however, generate only a limited amount of ions. An attempt has been made in which a plurality of ion generators are provided so as to increase the amount of generated ions. In such a case, placement of ion generators in an air-flowing path, which is suitable for ion generation, causes a number of space constraints including safety requirements. In order to house a plurality of ion generators in such a limited space, collective arrangement of ion generators is preferred.

[Patent Document 1] Japanese Unexamined Patent Application Publication No. 2002-257408
[Patent Document 2] Japanese Unexamined Patent Application Publication No. 2007-114177
[Patent Document 3] Japanese Unexamined Patent Application Publication No. 2008-059795
[Patent Document 4] Japanese Unexamined Patent Application Publication No. 2008-123917

SUMMARY OF THE INVENTION

Problem to be Solved by the Invention

With the conventional air purifying apparatus, the amount of ions generated by an ion generating section and the amount of ions in a room discharged from the discharge port together with the air are measured, resulting that the amount of ions in the room is smaller compared to the amount of ions generated by the ion generating section.

The present invention has been contrived in view of the above circumstances. A main object of the invention is to provide an ion generating apparatus and an air purifying apparatus including an ion generating section arranged at a laminar flow section where flow of the air suctioned by an air blower becomes laminar flow so that the air suctioned by the air blower may effectively include ions generated by the ion generating section, reducing the difference between the amount of ions generated by the ion generating section and the amount of ions in a room, increasing the amount of ions in the room.

When, however, an ion generator is operated for a long period of time, causing that a discharge electrode is worn due to sputter evaporation associated with corona discharge, or when foreign materials such as chemicals or dusts are accumulated and attached to the discharge electrode, problems arise such that the amount of generated ions decreases and the ion generator reaches the end of product lifetime. Though regular maintenance and lifetime control are required for the ion generator in order to secure stabilized generation of ions, it is desirable for the ion generator to be free from maintenance.

The present invention has been contrived in view of the above circumstances and has an object of providing: an ion generating apparatus in which a plurality of ion generators are intermittently driven to extend the operational lifetime without much decrease in the amount of ions dispersed in a space where ions are discharged; and an air purifying apparatus including the ion generating apparatus.

When, however, a plurality of ion generators are collectively arranged adjacent to one another, mutual interference may occur, possibly reducing ion generation efficiency as the entire ion generator.

The present invention has been contrived in view of the above circumstances and has an object of providing: an ion generating apparatus in which a plurality of ion generators are arranged in a biased manner to suppress mutual interference even when the ion generators are collectively arranged, alleviating reduction in efficiency of ion generation; and an air purifying apparatus including the ion generating apparatus.

Means for Solving the Problem

In an ion generating apparatus according to the present invention, in an air purifying apparatus including a housing having a suction port and a discharge port, an air blower housed in the housing, a filter that lets through air suctioned from the suction port by the air blower, and an ion generating section that generates ions, and discharging the ions generated by the ion generating section from the discharge port together with the air suctioned by the air blower, the ion generating section is arranged in a laminar flow section where flow of the air becomes laminar flow.

According to the invention, the ions generated by the ion generating section can be included in the air at the laminar flow section formed to make the flowing air laminar flow, allowing the air to efficiently include the ions generated by the ion generating section, increasing the amount of ions included in the air, and increasing the amount of ions discharged into a room. Hence, purification of the room air can further be enhanced.

Moreover, the ion generating apparatus according to the present invention is preferably configured such that the air blower has an impeller, that the ion generating apparatus comprises a rectification body that rectifies airflow generated by rotation of the impeller, and that the ion generating section is arranged at the rectification body.

According to the invention, the air rectified by the rectification body and passing through as laminar flow can efficiently include ions, further increasing the amount of ions discharged from the discharge port together with the air.

Moreover, the ion generating apparatus according to the present invention is preferably configured such that the rectification body is a casing that houses the impellers.

According to the invention, the air of laminar flow passing through a comparatively narrow path in the casing can include ions, allowing the air to efficiently include ions generated by the ion generating section, further increasing the amount of ions discharged from the discharge port together with the air.

The ion generating apparatus according to the present invention is preferably configured such that the air blower has an impeller and a casing that houses the impeller, that the ion generating apparatus includes an air-flowing path arranged between the casing and the discharge port to let through the air toward the discharge port, and that the ion generating section is arranged at the air-flowing path and the casing.

According to the invention, the air of laminar flow that passes through a comparatively narrow path in the casing can include ions, and the air blown out to the air-flowing path from the blowing port of the casing can further include the ions generated by the ion generating section. This allows the air to more efficiently include the ions generated by the ion generating section, further increasing the amount of ions discharged from the discharge port together with the air.

The ion generating apparatus according to the present invention is preferably configured such that the casing has a circular-arc guide wall that guides airflow generated by rotation of the impeller and a blowing port opened from a part of the circular-arc guide wall to one direction of a tangent line of the circular-arc guide wall, and that the ion generating section is arranged at the circular-arc guide wall.

According to the invention, the air of laminar flow passing through a comparatively narrow path in the casing at high wind speed can include ions. Hence, the air can more efficiently include ions generated by the ion generating section, further increasing the amount of ions discharged from the discharge port together with the air.

The ion generating apparatus according to the present invention is preferably configured such that more than one of the ion generating sections are arranged separately from each other in a direction intersecting with an air-flowing direction in which the air passes through.

According to the invention, the number of portions where the air of laminar flow includes ions in a comparatively narrow path in the casing can be increased. Hence, the ions generated by the ion generating section can more effectively be included in the air, further increasing the amount of ions discharged from the discharge port together with the air.

The ion generating apparatus according to the present invention is preferably configured such that more than one of the ion generating sections are arranged at positions separated from each other in the air-flowing direction and biased relative to each other in a direction intersecting with the air-flowing direction.

According to the invention, the number of portions where the air of laminar flow can include ions in a comparatively narrow path in the casing can be increased with the conventional casing. Hence, the air can more efficiently include ions generated by the ion generating section, further increasing the amount of ions discharged from the discharge port together with the air.

The ion generating apparatus according to the present invention is preferably configured such that the ion generating sections are so arranged as not to overlap with each other in the air-flowing direction.

According to the invention, the air of laminar flow can include the ions generated by the ion generators without cancelling each other out, allowing the air to more efficiently include ions, further increasing the amount of ions discharged from the discharge port together with the air.

The ion generating apparatus according to the present invention is preferably configured to comprise a holder that holds each of the ion generating sections, wherein the holder curves in the air-flowing direction and has a curved surface on which a portion corresponding to each of the ion generating sections is opened, and each of the ion generating sections is arranged at the opening of the curved surface.

According to the invention, the curved surface of the holder can be in contact with the circular-arc guide surface that guides the airflow generated by rotation of the impellers in the casing, allowing the plurality of ion generating sections to have the same shape and the amount of ions generated by the ion generators to be equal to each other.

An air purifying apparatus according to the present invention comprises the ion generating apparatus described above.

According to the invention, the ions generated by the ion generating section can be included in the air at the laminar flow section formed such that the passing air becomes laminar flow. Hence, the air can efficiently include the ions generated by the ion generating section, increasing the amount of ions included in the air, increasing the amount of ions discharged into the room, and further enhancing purification of the room air.

An ion generating apparatus according to the invention, comprising a driving circuit that drives a plurality of ion generators which generate ions, is characterized in that the driving circuit drives the ion generators periodically in different phases.

According to the invention, the driving circuit drives the plurality of ion generators periodically in different phases.

This prevents each ion generator from being affected by the ions generated by another ion generator (hereinafter referred to as interference), while reducing the rate of energization and thus extending operational lifetime.

In the ion generating apparatus according to the present invention, at least one of the plurality of ion generators is separated from another ion generator.

According to the invention, at least one ion generator is arranged separately from another ion generator.

By thus separating at least the most-frequently-driven ion generator from another ion generator when a plurality of ion generators are driven in different phases, the rate of reduction in the amount of generated ions due to the ion generators interfering with each other is lowered.

The ion generating apparatus according to the present invention comprises an air-blowing fan that blows ions generated by the plurality of ion generators to the outside.

According to the present invention, the air-blowing fan blows out the ions generated by the plurality of ion generators to the outside.

This prevents the generated ions from remaining in the vicinity of the ion generators and prevents the amount of generated ions from decreasing, while further suppressing the ion generators interfering with each other and also efficiently leading the generated ions to the outside.

The ion generating apparatus according to the present invention comprises two of the ion generators, wherein the driving circuit alternately drives the ion generators.

According to the invention, the driving circuit alternately drives the two ion generators.

Hence, when the ion generators are alternately driven at cycles in which the amount of ions generated by the two ion generators becomes maximum, there is no large difference in the amount of generated ions compared to the case where two ion generators are continuously driven, while the operational lifetime of the ion generating apparatus using the ion generators is doubled.

An air purifying apparatus according to the present invention comprises: an ion generating apparatus according to one of the inventions described above; and a purifier that purifies the air which is to include ions generated by the ion generating apparatus.

According to the invention, the air purified by the purifier can include the ions generated by the ion generating apparatus according to any one of the inventions described above.

Hence, an ion generating apparatus in which mutual effects of the plurality of ion generators are suppressed and the operational lifetime of each ion generator is extended can be applied to an air purifying apparatus.

As described above, it has conventionally been known that $H^+(H_2O)_m$ (m is an arbitrary natural number), which is a positive ion, and $O_2^-(H_2O)_n$ (n is an arbitrary natural number), which is a negative ion, sterilize floating bacteria or the like in the air by reaction of ions. The ions, however, recombine with each other and disappear. Thus, even if high concentration of ions can be realized in the proximity of the ion generator, the concentration thereof is rapidly lowered as the distance from the ion generator becomes farther. Hence, even if the concentration of ions can be several tens of thousands/$cm^3$ in a small-volume space such as an experimental apparatus, only two to three thousand ions/$cm^3$ at the most can be achieved in a large-volume space such as an actual residential space or work space.

The inventors, on the other hand, have found that bird influenza virus can be removed, in an experimental laboratory level, by 99% in ten minutes when the ion concentration of 7,000 ions/$cm^3$ is achieved and by 99.9% when that of 50,000 ions/$cm^3$ is achieved. These numbers of removal rates mean that, if there are 1,000 viruses/$cm^3$ in the air, 10 virus/$cm^3$ and 1 virus/$cm^3$ remain, respectively. In other words, by increasing the ion concentration from 7,000 ions/$cm^3$ to 50,000 ions/$cm^3$, the remaining viruses will be reduced to one tenth. This shows that it is very important for protection against infectious diseases and environmental purification to increase the ion concentration in the entire residential space or work space where a person or the like lives.

An ion generating apparatus according to the present invention is based on the knowledge described above, comprising a plurality of ion generators in which positive and negative ion generating sections that generate ions are arranged in a juxtaposed manner, and is characterized in that the plurality of ion generators are biased such that juxtaposed direction of the positive and negative ion generating sections in each ion generator is aligned and the ion generating sections do not overlap with each other in the juxtaposed direction.

According to the invention, the ion generating sections are not overlapped with each other in the juxtaposed direction. Thus, when the ion generating apparatus is arranged in the air-flowing path such that the juxtaposed direction is approximately vertical to the direction of the airflow passing through near each ion generating section, ions generated by the ion generating sections are prevented from overlapping and interfering with each other.

In the ion generating apparatus according to the present invention, the plurality of ion generators are arranged in a direction intersecting with the juxtaposed direction, and each of the ion generating sections generates ions toward one side in a direction vertically intersecting with the arrangement direction.

According to the invention, ions are generated to one side of the direction vertically intersecting with the arrangement direction of the ion generators. Hence, when the ion generating apparatus is placed in the air-flowing path such that the arrangement direction is approximately in parallel with the direction of airflow passing through near the ion generating sections, the ions generated by the ion generating sections efficiently pass through the air-flowing path together with the airflow.

In the ion generating apparatus according to the present invention, the ion generator includes an opening for each of the positive and negative ion generating sections, and a bias amount of the ion generators in the juxtaposed direction is equal to or larger than a length of the opening in the juxtaposed direction.

According to the invention, the openings of the ion generating sections do not overlap with each other in the juxtaposed direction. Thus, when the ion generating apparatus is arranged in the air-flowing path such that the juxtaposed direction is approximately perpendicular to the direction of airflow passing through near the openings of the ion generating sections, ions generated by the ion generating sections are prevented from overlapping and interfering with each other.

In the ion generating apparatus according to the present invention, the ion generators are biased toward one side in the juxtaposed direction, and a total amount of bias for the ion generators in the juxtaposed direction is equal to or smaller than a separation distance between the positive and negative ion generating sections.

According to the invention, the positive ion generating sections and the negative ion generating sections are placed separately from each other on both sides of the juxtaposed direction. Thus, when the ion generating apparatus is placed in the air-flowing path such that the juxtaposed direction is approximately perpendicular to the direction of airflow passing through near the ion generating sections, positive and negative ions generated by the ion generating sections are prevented from overlapping and interfering with each other.

An air purifying apparatus according to the present invention comprises: the ion generating apparatus according to any one of the inventions described above; and a purifier that purifies air which is to include the ions generated by the ion generating apparatus.

According to the invention, the air purified by the purifier is made to include ions generated by the ion generating apparatus according to the inventions described above. Hence, the ion generating apparatus that suppresses overlapping and mutual interference of ions generated by a plurality of ion generating sections may be applied to an air purifying apparatus.

Effects of the Invention

According to the present invention, the ions generated by the ion generating section can be included in the air at the laminar flow section where the flowing air becomes laminar flow, allowing the air to efficiently include the ions generated by the ion generating section and increasing the amount of ions included in the air. Hence, the amount of ions discharged into a room can be increased.

According to the present invention, a plurality of ion generators are periodically driven in different phases. This prevents each ion generator from being affected by the ions generated by another ion generator while the rate of energization decreases, extending the operational lifetime as an ion generating apparatus. Hence, the operation lifetime can be extended without much decrease in the amount of ions dispersed in the space where ions are discharged.

According to the present invention, when the ion generating apparatus is placed in the air-flowing path such that the juxtaposed direction of the ion generating sections is approximately perpendicular to the direction of airflow passing through near the ion generating sections, the ions generated by the ion generating sections are prevented from overlapping and interfering with each other.

This can prevent mutual interference of ions and can alleviate decrease in ion generation efficiency, even when the ion generators are arranged in a collective manner.

BRIEF DESCRIPTION OF THE DRAWINGS

FIG. 13 is a table illustrating an example of measurement in a room for ion concentration and ion balance when one ion generator is constantly turned on (driven) and when it is alternately turned on and off, and for ratio of ion concentration obtained when the ion generator is constantly turned on to ion concentration obtained when it is alternately turned on and off.

FIG. 15 is a table illustrating an example of measurement in a room for ion concentration and ion balance when two ion generators are constantly turned on and when they are alternately turned on and off, and for ratio of ion concentration obtained when the ion generators are constantly turned on to ion concentration obtained when they are alternately turned on and off.

Figure 1:
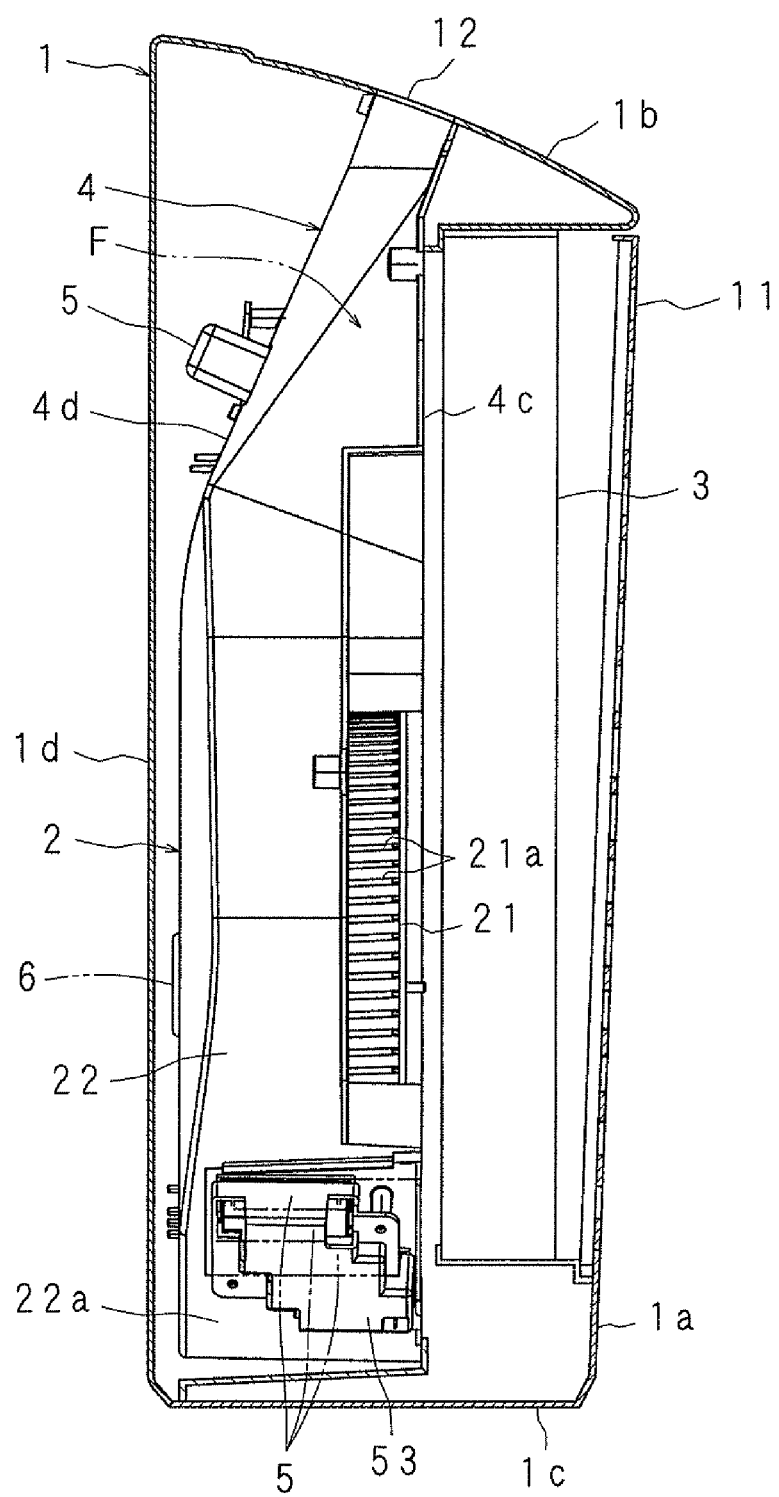
FIG. 1 is a vertical section side view illustrating the configuration of an air purifying apparatus according to the present invention.

DESCRIPTION OF REFERENCE CHARACTERS 1 housing
11 suction port
12 discharge port
2 air blower
21 impeller
22 casing
22*a* circular-arc guide wall
22*b* blowing port 3 filter
4 duct
5 ion generator
51, 52 ion generating section
53 holder
F laminar flow section
2 air blower
3 filter (purifier)
4 duct
5 ion generator
6 motor
12 discharge port
21 impeller (air-blowing fan)
22 casing
30 CPU
31 ROM
32 RAM
33 timer
37 air-blower driving circuit
38 ion generator driving circuit (driving circuit)
1 housing
2 air blower
3 filter (purifier)
4 duct
5 ion generator
6 motor
11 suction port
12 discharge port
21 impeller
22 casing
22a circular-arc guide wall
51, 52 ion generating section (positive and negative ion generating section)
51a, 52a opening
500 ion generating apparatus
501 holder
L3 opening length
L4, L5, L6 amount of bias

DETAILED DESCRIPTION OF THE INVENTION

Embodiment 1

Figure 2:
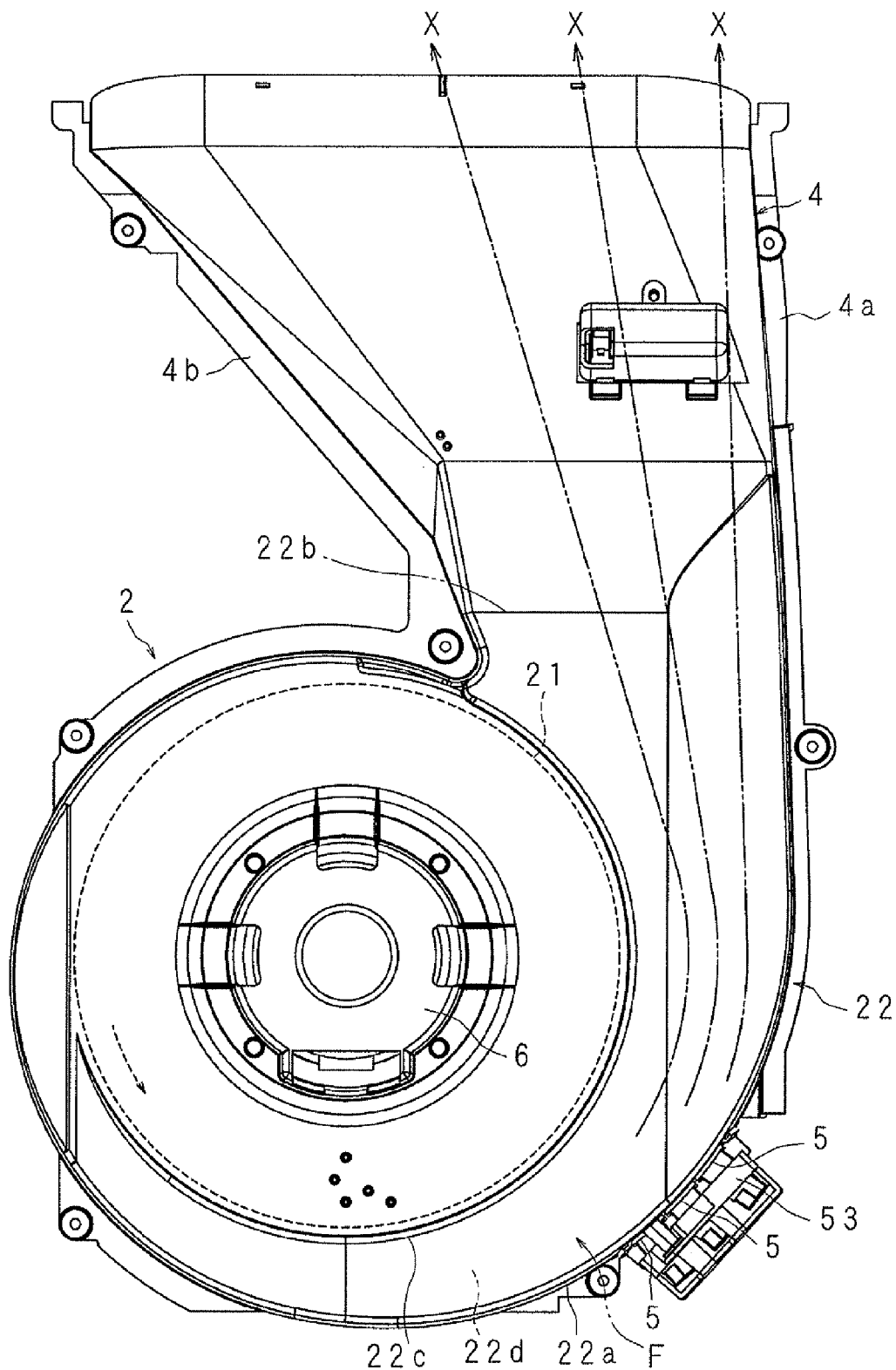
FIG. 2 is a front view illustrating the configuration of a main part of an air purifying apparatus according to the present invention.
Figure 3:
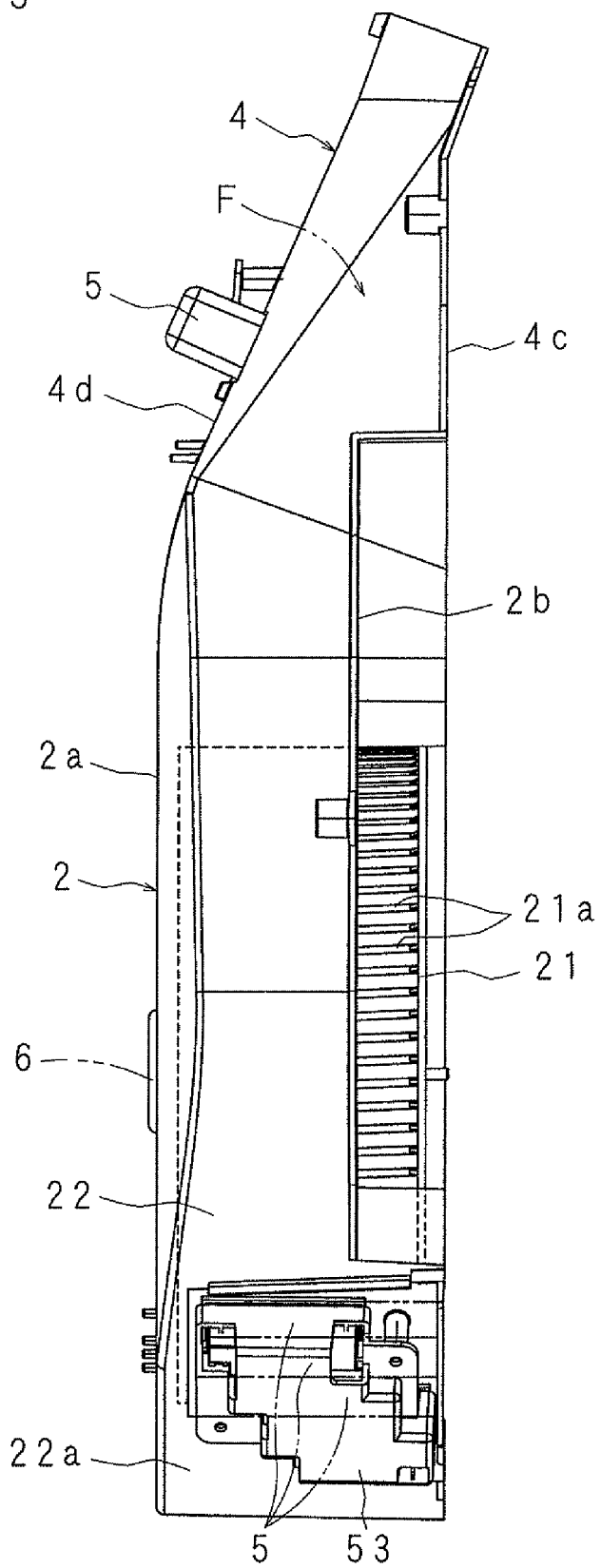
FIG. 3 is a side view illustrating the configuration of a main part of an air purifying apparatus according to the present invention.
Figure 4A:
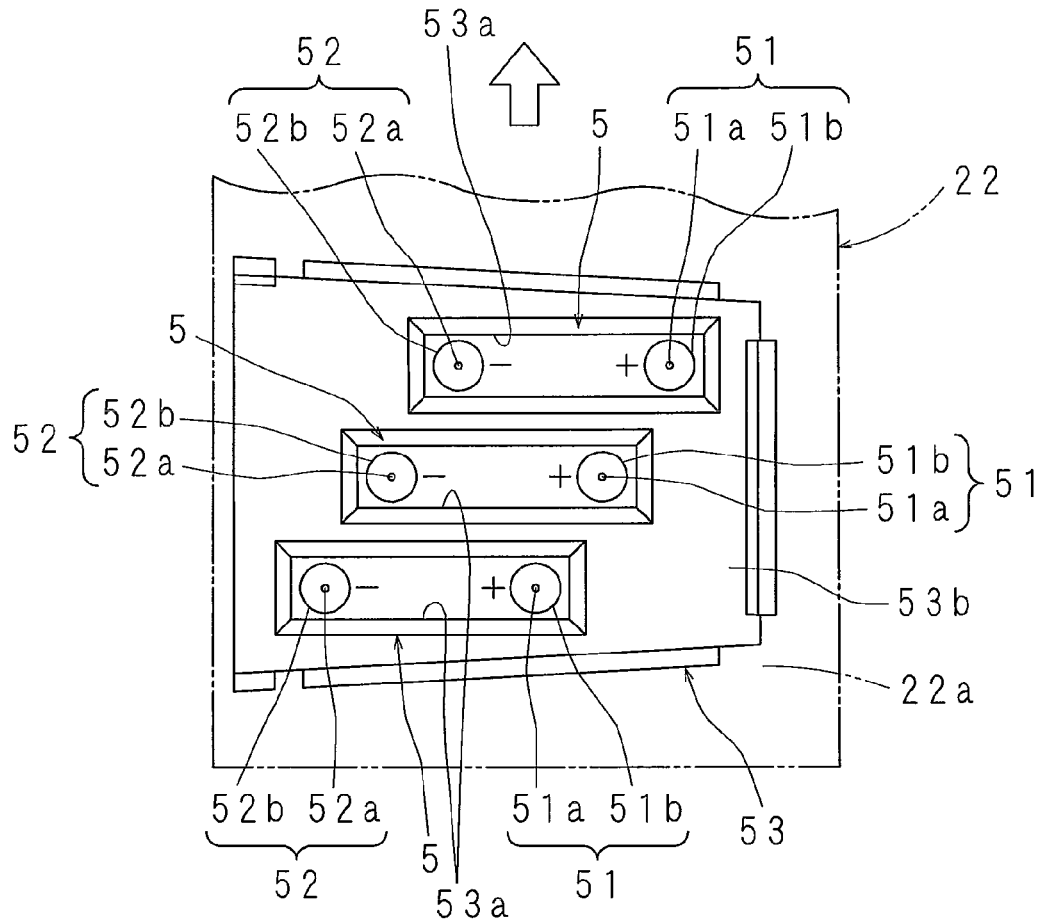
FIG. 4 illustrates (a) a front view and (b) a side view of the configuration of an ion generator in an air purifying apparatus according to the present invention.
Figure 4B:
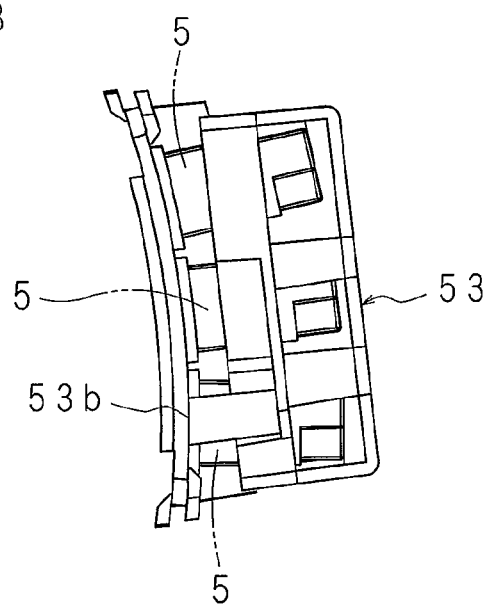

The present invention will be described in detail based on the drawings illustrating an embodiment thereof. Here, an air purifying apparatus is described as an example. FIG. 1 is a vertical section side view illustrating the configuration of an air purifying apparatus according to the present invention. FIG. 2 is a front view illustrating the configuration of a main part, FIG. 3 is a side view illustrating the configuration of a main part, and FIG. 4 illustrates a front view of the configuration of an ion generator and FIG. 4B illustrates a side view of the configuration of an ion generator.

The air purifying apparatus illustrated in FIG. 1 includes: a housing 1 having a suction port 11 on a back wall 1a and having a discharge port 12 on a top wall 1b; an air-blower 2 arranged at a lower part in the housing 1; a filter 3 arranged inside of the suction port 11 to let through the air suctioned from the suction port 11 by the air blower 2 while eliminating foreign materials in the air to clean the air; a duct 4 arranged between the air blower 2 and the discharge port 12 and formed as an air-flowing path that lets through the air to the discharge port 12; and an ion generator 5 having two ion generating sections 51 and 52, which make the air blown by the air blower 2 include positive and negative ions. The air purifying apparatus is configured to make the air blown by the air blower 2 include positive and negative ions generated by the ion generating sections 51 and 52, and to discharge the positive and negative ions from the discharge port 12 to the outside together with the air.

The housing 1 forms an approximately rectangular parallelepiped having a bottom wall 1c with a shape of a rectangle (quadrangle) in planar view, a front wall 1d continuing into two sides of the bottom wall 1c, side walls continuing into the other two sides of the back wall 1a and the bottom wall 1c, and a top wall 1b. The suction port 11 of a rectangular shape with its longitudinal direction being top and bottom is provided on the back wall 1a, while the discharge port 12 of a rectangular shape with its longitudinal direction being on the side of the both side walls is provided on the top wall 1b.

The air blower 2 forms a cylindrical and centrifugal shape having an impeller 21 with its rotation shaft arranged back and forth, and a casing 22 in which the impeller 21 is housed to be rotatable. A motor 6 which drives the impeller 21 is attached to the front side portion of the casing 22.

The impeller 21 is a multi-blade impeller having a plurality of blades 21a with the side of its rotating center displaced in the rotating direction relative to the outer edge. In other words, it is a Sirocco impeller (Sirocco fan) having a circular-cylindrical shape. One end of the impeller 21 has a bearing board. The output shaft of the motor 6 is attached to a shaft hole opened at the center of the bearing board, which functions such that the air taken in from an opening at the other end to an air hole at the center is released from between the blades 21a on the outer circumference.

The casing 22 has a circular-arc guide wall 22a that guides the airflow generated by rotation of the impeller 21 in the rotating direction to increase the speed of the airflow, a blowing port 22b opened upward from a part of the circular-arc guide wall 22a to one direction of the tangent line of the circular-arc guide wall 22a, and a circular-arc partition wall 22c arranged between the circumferential surface of the impeller 21 and the circular-arc guide wall 22a. The blowing port 22b forms a square-tubular shape that protrudes from a part of the circular-arc guide wall 22a in the direction of the tangent line of the circular-arc guide wall 22a. Moreover, the casing 22 forms the shape of a deep dish, including a casing body 2a having the circular-arc guide wall 22a, the circular partition wall 22c and an opening for a blowing port 22b, and including a cover plate 2b on which the portion corresponding to the opening of the impeller 21 is opened and which closes the open side of the casing body 2a, the cover plate 2b being attached to the casing body 2a with a plurality of male screws. The circular-arc guide wall 22a constitutes a rectification body that rectifies the airflow generated by rotation of the impeller 21. A circular-arc air-flowing path 22d between the circular-arc guide wall 22a and the circular-arc partition wall 22c forms a laminar flow section F.

Thus formed circular-arc guide wall 22a of the casing 2 has a penetration hole corresponding to the ion generating sections 51 and 52 as well as an attachment hole separately arranged from the penetration hole, the ion generator 5 being attached by a male screw which is screwed into the attachment hole.

The duct 4 forms a square-tubular shape with its lower end continuing into the blowing port 22b and its upper end being opened, and is integrally formed with the casing body 2a and the cover plate 2b. Moreover, the duct 4 includes one side wall 4a arranged along one direction of the tangent line of the circular-arc guide wall 22a from the blowing port 22b, another side wall 4b with a separation distance from the one side wall gradually increasing from the blowing port 22b, a back wall 4c continuing into the one side wall 4a and another side wall 4b and vertically arranged, and a front wall 4d with a separation distance from the back wall 4c gradually decreases from the blowing port 22b. The duct 4 is configured to have the laminar flow section F on the side facing the impeller 21 of the front wall 4d, and to guide the air blown out from the blowing port 22b to form laminar flow along the one side wall 4a, back wall 4c and front wall 4d. Moreover, on the front wall 4d, a penetration hole corresponding to the ion generating sections 51 and 52 as well as an attachment hole which is separated from the penetration hole are opened. The ion generator 5 is engaged into the penetration hole on the front wall to be facing the laminar flow section F and is fixed by a male screw which is inserted into the attachment hole.

The ion generator 5 includes: two ion generating sections 51 and 52 that are separated from each other in a direction intersecting with the flowing direction of the air sent by the air blower 2; a power feeding section that supply voltage to the ion generating sections 51 and 52; and a holder 53 that holds the ion generating sections 51, 52 and the power feeding section. The ion generator 5 is configured such that the power feeding section supplies voltage to the ion generating sections 51 and 52 so that the ion generating sections 51 and 52 cause corona discharge to generate ions.

The ion generating sections 51 and 52 have discharge electrode convex sections 51a and 52a having peaked shapes as well as dielectric electrode rings 51b and 52b that enclose the discharge electrode convex sections 51a and 52a, which are arranged at the central parts of the dielectric electrode convex sections 51b and 52b, respectively. The ion generator 5 is configured such that one ion generating section 51 generates positive ions while the other ion generating section 52 generates negative ions.

The ion generating section 5 is attached to the circular-arc guide wall 22a constituting the rectification body of the casing 22 and on the front wall 4d of the duct 4, and has two ion generating sections 51 and 52 arranged at a position intersecting with the flowing direction of the air.

For the ion generator 5 attached to the circular-arc guide wall 22a of the casing 22, three of them are held by one holder 53. The three ion generators 5 are juxtaposed separately from one another in the air-flowing direction (the arc direction of the circular-arc guide wall 22a) and are relatively biased in a direction intersecting with the air-flowing direction (the direction of the rotation shaft of the impeller 21). Moreover, the ion generating sections 51 and 52 of the three ion generators 5 are arranged such that the polarity is made equal in the relatively-biased direction while there is no overlapping in the air-flowing direction. The ion generating sections 51 and 52 of each ion generator 5 face the casing 22 from the penetration hole. Furthermore, the attachment side of the holder 53 to the casing 22 is curved toward the air-flowing direction, having a curved surface 53b on which three portions are opened, each corresponding to the ion generating sections 51 and 52, which are arranged at an opening 53a of the curved surface 53b.

The air purifying apparatus constituted as above is installed near a wall in a residential room such that the suction opening 11 comes on the side of the wall.

The air blower 2 is driven to rotate the impeller 21, which causes the suction port 11 to suction the air in the room into the housing 1 and generates an air-flowing path between the suction port 11 and the discharge port 12, while the filter 3 eliminates foreign materials such as dust in the suctioned air to produce clean air.

The air passed through the filter 3 is suctioned into the casing 22 of the air blower 2. Here, the air suctioned into the casing 22 becomes the airflow along the circular-arc partition wall 22c around the impeller 21 while being sent to the circular-arc air-flowing path 22d between the circular-arc partition wall 22c and the circular-arc guide wall 22a. The airflow is rectified by the circular-arc guide wall 22a and becomes laminar flow at the laminar flow section F of the circular-arc air-flowing path 22d. The air passing through as laminar flow at the laminar flow section F is guided along the circular-arc guide wall 22a to the blowing port 22b as indicated by the arrows X of dashed double-dotted lines in FIG. 2 and is blown out into the duct 4 from the blowing port 22b.

The ion generating sections 51 and 52 are arranged on the circular-arc guide wall 22a of the casing 22 in the air blower 2, so that the ions generated by the ion generating sections 51 and 52 can effectively be included in the air of laminar flow passing through in a comparatively-narrow path of the laminar flow section F along the circular-arc guide wall 22a. Moreover, the air passing through along the circular-arc guide wall 22a flows at high wind speed, allowing the air to more effectively include ions.

Furthermore, the ion generator 5 has two ion generating sections 51 and 52 at a position intersecting with the flowing direction of the air to increase the number of portions where the air includes ions for the first time, allowing the air to more effectively include ions.

Moreover, three ion generators 5 are arranged separately from one another in the air-flowing direction of clean air while the three ion generators 5 are relatively biased in a direction intersecting with the air-flowing direction so as to avoid overlapping of the ion generating sections 51 and 52 of the ion generators 5 in the air-flowing direction. Such arrangement of the ion generators 5 increases the number of portions where the air includes ions for the first time and prevents positive ions and negative ions generated by the ion generating sections 51 and 52 in the ion generators 5 from canceling each other out. Accordingly, ions can more effectively be included in the air without increase in the size of the casing 22.

The positive and negative ions included in the air passing through as laminar flow as described above are mixed together when the air is blown into the duct 4 from the blowing port 22b of the casing 22.

The duct 4 is configured such that the air passes through as laminar flow along the one side wall 4a, back wall 4c and front wall 4d, the front wall 4d that makes the air pass through as laminar flow having ion generating sections 51 and 52 thereon. Hence, the air in which positive and negative ions are included in the casing 22 in the air-blower 2 can further include the positive and negative ions generated by the ion generating sections 51 and 52 arranged at the duct 4, increasing the amount of ions in the air.

Figure 5:
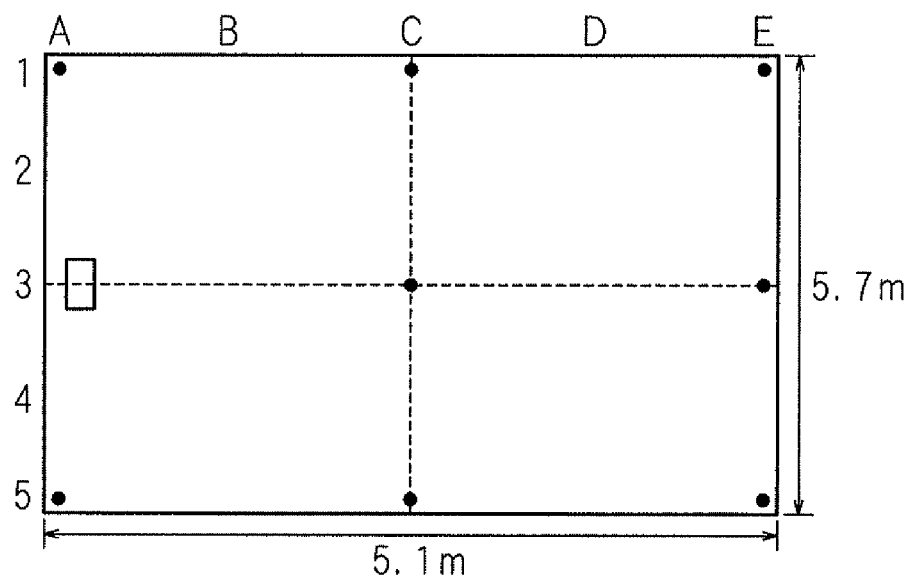
FIG. 5 is a layout of measurement performed in a room of the air blown out from a discharge port of an air purifying apparatus according to the present invention installed on a floor in the room.
Figure 6:
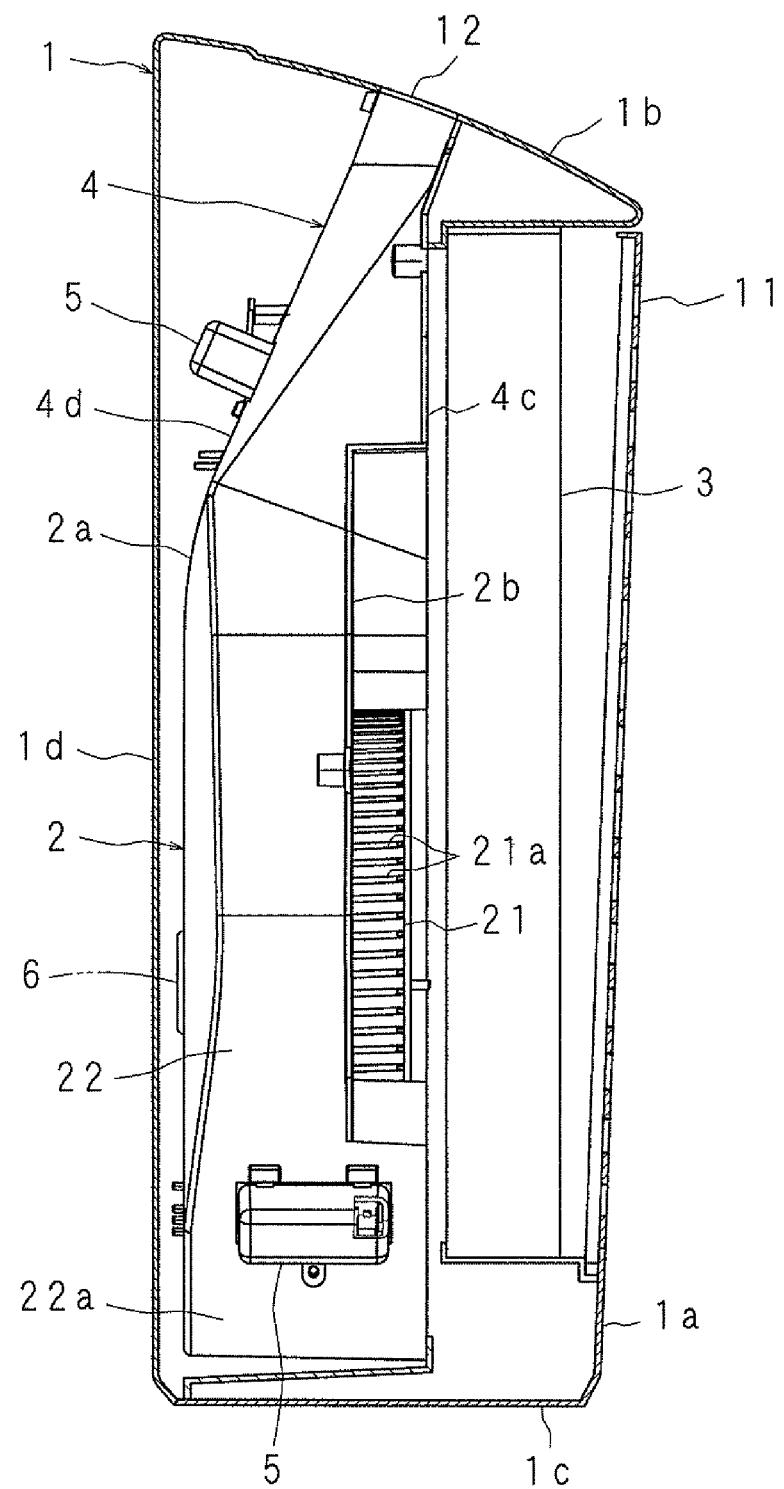
FIG. 6 is a vertical section side view illustrating the configuration of an air purifying apparatus according to an embodiment of the present invention.
Figure 7:
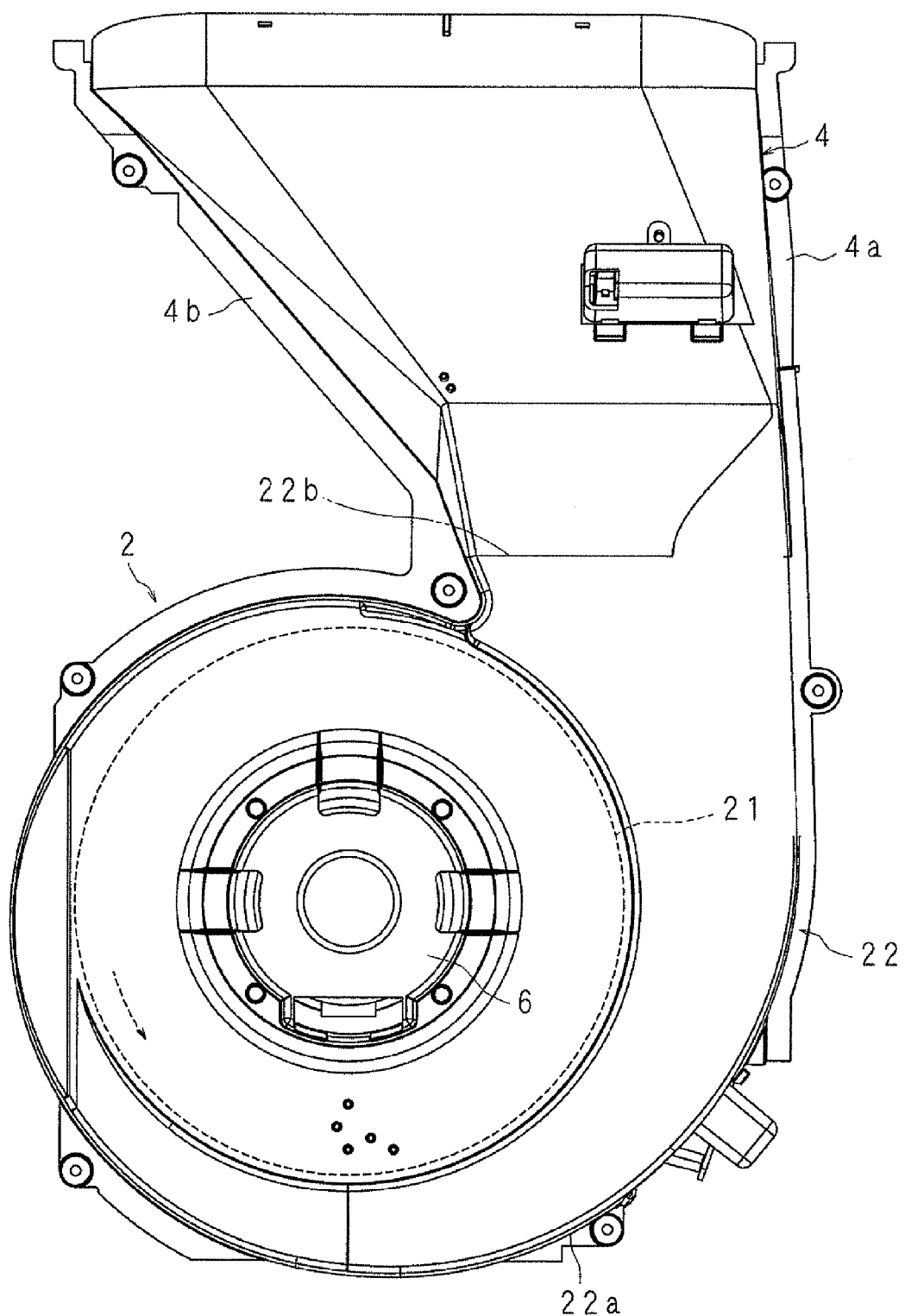
FIG. 7 is a front view illustrating the configuration of a main part.
Figure 8:
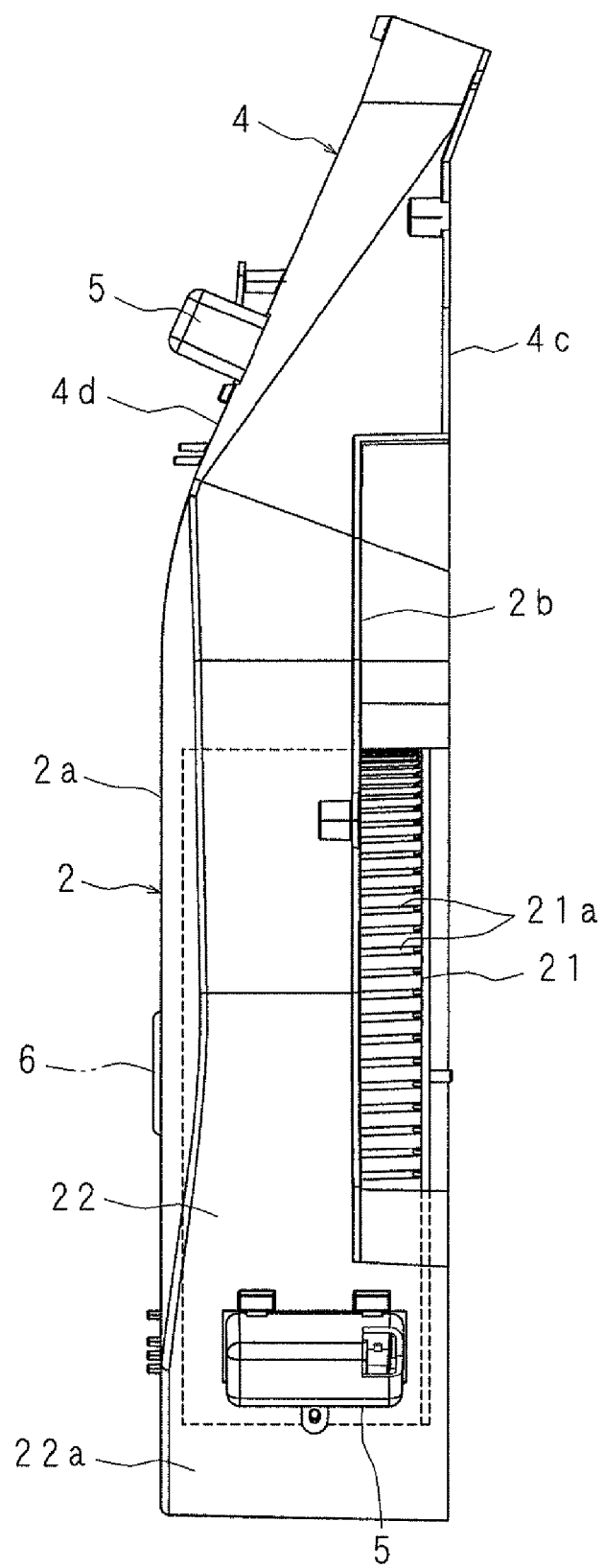
FIG. 8 is a side view illustrating the configuration of a main part.

FIG. 5 is a layout of measurement performed in a room for the air blown out from a discharge port of an air purifying apparatus according to the present invention installed on a floor in a room. Table 1 shows data indicating the result obtained by measuring the amount of ions in a room. When the amount of ions was measured at A to E points in the room for the conventional air purifying apparatus including an ion generator and for the air purifying apparatus according to the present invention, the result shown in Table 1 was obtained. In FIG. 5, the room has a floor space of 5.1 m×5.7 m while the air purifying apparatus is installed on the floor separated by 0.3 m from one wall on the 5.7 m side. The measurement point A is positioned at a portion separated by 0.1 m from one wall of the 5.1 m side in the room, including points 1, 3 and 5 on the 5.7 m side. The measurement point C is positioned at the center of the 5.1 m side in the room, including points 1, 3 and 5 on the 5.7 m side. The measurement point E is positioned at a portion separated by 0.1 m from the other wall of the 5.1 m side in the room, including points 1, 3 and 5 on the 5.7 m side. Moreover, the measurement time is for twenty minutes from the start of blowing out, while the amount of ions corresponds to the number of positive ions (number of ions/cm$^3$) and the number of negative ions (number of ions/cm$^3$) in the air.

TABLE 1

| MEASUREMENT POINT | (+)ION (NUMBER OF IONS/cm$^3$) | (−)ION (NUMBER OF IONS/cm$^3$) | STERILIZATION ION(NUMBER OF IONS OF IONS/cm$^3$) |
| --- | --- | --- | --- |
| A1 | 49,000 | 47,000 | 47,000 |
| A3 | 300,000 | 340,000 | 63,500 |
| A5 | 80,000 | 90,000 | 80,000 |
| C1 | 32,000 | 34,000 | 32,000 |
| C3 | 15,000 | 18,000 | 15,000 |
| C5 | 47,000 | 57,000 | 47,000 |
| E1 | 18,000 | 18,000 | 18,000 |
| E3 | 27,000 | 33,000 | 27,000 |
| E5 | 27,000 | 30,000 | 27,000 |
| AVERAGE NUMBER IN MEASUREMENT POINTS | 66,111 | 74,111 | 39,611 |
| INCREASE RATE % | | | 154 |

NOTE THAT THE MEASUREMENT POINT A3 CORRESPONDS TO AN AVERAGE VALUE OF A1 AND A5.

From the measurement result shown in Table 1, the average amount of sterilization ions at the measurement points is 39,611 (ions/cm$^3$), the increasing rate being 154%. This verified that the amount of ions discharged in the room can be increased.

Furthermore, it has conventionally been known that H$^+$(H$_2$O)$_m$ (m is an arbitrary natural number), which is a positive ion, and O$_2^-$(H$_2$O)$_n$ (n is an arbitrary natural number), which is a negative ion, are sent out in the air to sterilize floating bacteria or the like by reaction of ions. The ions, however, recombine with each other and disappear. Thus, even if high concentration of ions can be realized in the proximity of the ion generating element, the concentration thereof is rapidly lowered as the distance from the ion generating element becomes farther. Hence, even if the concentration of ions can be several tens of thousands/cm$^3$ in a small-volume space such as an experimental apparatus, only two to three thousand ions/cm$^3$ at the most can be achieved in a large-volume space such as an actual residential space or work space.

The inventors, on the other hand, have found that bird influenza virus can be removed, in an experimental laboratory level, by 99% in ten minutes when the ion concentration of 7,000 ions/$cm^3$ is achieved and by 99.9% when that of 50,000 ions/$cm^3$ is achieved. These numbers of removal rates mean that, if there are 1,000 viruses/$cm^3$ in the air, 10 virus/$cm^3$ and 1 virus/$cm^3$ remain, respectively. In other words, by increasing the ion concentration from 7,000 ions/$cm^3$ to 50,000 ions/$cm^3$, the remaining viruses will be reduced to one tenth.

This shows that it is very important for protection against infectious diseases and environmental purification to not only send out highly-concentrated ions but also increase the ion concentration in the entire residential space or work space where a person or the like lives.

Note that, in the embodiment described above, three ion generators 5 are arranged on the circular-arc guide wall 22*a* of the casing having the laminar flow section F where the flowing air becomes laminar flow, while one ion generator 5 is arranged on the front wall 4*d* of the duct 4 having the laminar flow section F where the flowing air becomes laminar flow. Additionally, the portion where the ion generator 5 is arranged is not particularly limited as long as the ion generator 5 is arranged at the laminar flow section F where the flowing air becomes laminar flow. For example, it may be arranged at least one of a portion continuing into the circular-arc guide wall 22*a* of the blowing port 22*b*, the circular-arc guide wall 22*a* and the front wall 4*d* of the duct 4.

Embodiment 2

An embodiment in which the ion generating apparatus according to the present invention is applied to an air purifying apparatus will be described below. FIG. 6 is a vertical section side view illustrating the configuration of an air purifying apparatus according to the present invention. FIG. 7 is a front view illustrating the configuration of a main part. FIG. 8 is a side view illustrating the configuration of a main part.

The air purifying apparatus illustrated in FIG. 6 includes: a housing 1 having a suction port 11 on a back wall 1*a* and a discharge port 12 on a top wall 1*b*; an air blower 2 arranged at a lower part in the housing 1; a filter (purifier) 3 arranged inside of the suction port 11 and letting through the air suctioned by the air blower 2 from the suction port 11 to eliminate foreign materials in the air and to produce clean air; a duct 4 arranged as an air-guiding path between the air blower 2 and the discharge port 12 to guide the clean air toward the discharge port 12; and an ion generator 5 that generates positive and negative ions in the clean air sent by the air blower 2. The air purifying apparatus is so configured as to discharge the positive and negative ions generated by the ion generator 5 to the outside from the discharge port 12 together with the clean air sent by the air blower 2.

The housing 1 forms an approximately rectangular-parallelepiped shape and has a bottom wall 1*c* forming a rectangle in planar view, a front wall 1*d* and a back wall 1*a* continuing into two sides of the bottom wall 1*c*, side walls continuing into the other two sides of the bottom wall 1*c*, and a top wall 1*b*. The suction port 11 forming a rectangle with its longitudinal direction being top and bottom is provided on the back wall 1*a*, while the discharge port 12 forming a rectangle with its longitudinal direction being on the sides of the both side walls.

The air blower 2 forms a cylindrical and centrifugal shape having an impeller (air-blowing fan) 21 with its rotation shaft arranged back and forth and a casing 22 in which the impeller 21 is housed to be rotatable. A motor 6 which drives the impeller 21 is attached to the front side portion of the casing 22.

The impeller 21 is a multi-blade impeller having a plurality of blades 21*a* with the side of its rotating center displaced in the rotating direction relative to the outer edge. In other words, it is a Sirocco impeller (Sirocco fan) having a circular-cylindrical shape. One end of the impeller 21 has a bearing board. The output shaft of the motor 6 is attached to a shaft hole opened at the center of the bearing board, which functions such that the air taken in from an opening at the other end to an air hole at the center is released from between the blades 21*a* on the outer circumference.

The casing 22 has a circular-arc guide wall 22*a* that guides the airflow generated by rotation of the impeller 21 in the rotating direction to increase the speed of the airflow, and a blowing port 22*b* opened upward from a part of the circular-arc guide wall 22*a* to one direction of the tangent line of the circular-arc guide wall 22*a*. The blowing port 22*b* forms a square-tubular shape that protrudes from a part of the circular-arc guide wall 22*a* in the direction of the tangent line of the circular-arc guide wall 22*a*. Moreover, the casing 22 forms the shape of a deep dish, including a casing body 2*a* having the circular-arc guide wall 22a and an opening for the blowing port 22b, and including a cover plate 2b on which the portion corresponding to the opening of the impeller 21 is opened and which closes the open side of the casing body 2a, the cover plate 2b being attached to the casing body 2a with a plurality of male screws.

Thus formed circular-arc guide wall 22a of the casing 22 has a penetration hole corresponding to the ion generator 5 as well as an attachment hole separately arranged from the penetration hole, the ion generator 5 being attached by a male screw which is screwed into the attachment hole.

The duct 4 forms a square-tubular shape with its lower end continuing into the blowing port 22b and its upper end being opened, and is integrally formed with the casing body 2a and the cover plate 2b. Moreover, the duct 4 includes one side wall 4a arranged along one direction of the tangent line of the circular-arc guide wall 22a from one side of the blowing port 22b, another side wall 4b with a separation distance from the one side wall gradually increasing from the other side of the blowing port 22b, a back wall 4c continuing into the one side wall 4a and another side wall 4b and arranged in the vertical direction, and a front wall 4d with a separation distance from the back wall 4c gradually decreases from the blowing port 22b. The duct 4 is configured to guide the clean air blown out from the blowing port 22b to form laminar flow along the one side wall 4a, back wall 4c and front wall 4d. On the front wall 4d, a penetration hole corresponding to the ion generator 5 and an attachment hole which is separated from the penetration hole are opened. The ion generator 5 is attached by a male screw inserted into the attachment hole.

The air purifying apparatus constituted as described above is installed near a wall in a residential room such that the suction port 11 comes on the wall side. The air blower 2 is driven to rotate the impeller 21. The air in the room is suctioned from the suction port 11 into the housing 1, generating an air-flowing path of wind between the suction port 11 and the discharge port 12. The filter 3 removes foreign materials such as dust in the suctioned air to produce clean air.

The clean air passed through the filter 3 is suctioned into the casing 22 of the air blower 2. Here, the circular-arc guide wall 22a around the impeller 21 causes the clean air suctioned into the casing 22 to be laminar flow. The laminar flow is guided along the circular-arc guide wall 22a toward the blowing port 22b, which blows the airflow into the duct 4. The circular-arc guide wall 22a of the casing 22 in the air blower 2 is provided with the ion generator 5, which generates ions in the clean air flowing through along the circular-arc guide wall 22a.

The duct 4 is configured to guide the clean air to be laminar flow along the one side wall 4a, back wall 4c and front wall 4d, while the ion generator 5 is arranged on the front wall 4d that guides the clean air to be laminar flow. Accordingly, in addition to the positive and negative ions generated in the clean air in the casing 22 of the air blower 2, the ion generator 5 arranged at the duct 4 increases the amount of positive and negative ions.

Figure 9:
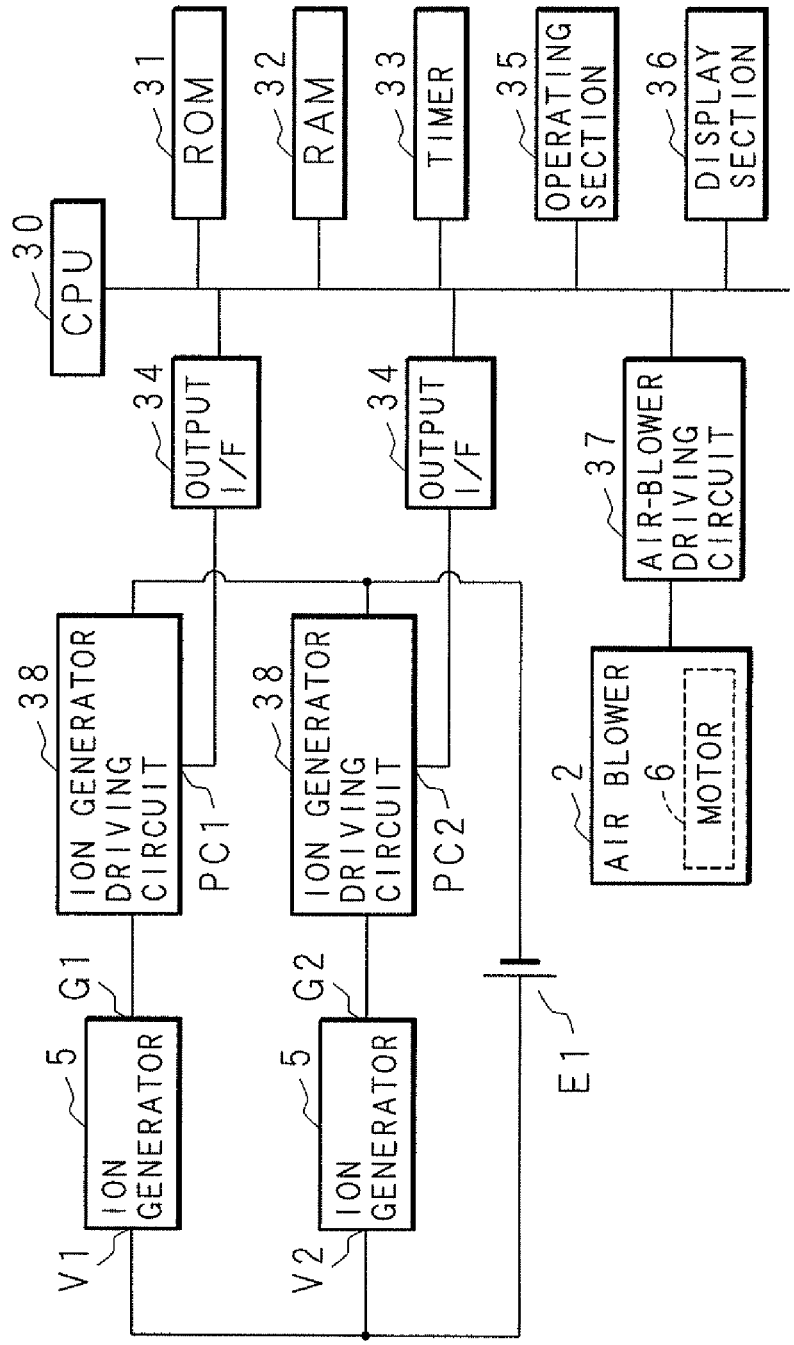
FIG. 9 is a block diagram illustrating schematic configuration of a control system of an air purifying apparatus.

FIG. 9 is a block diagram illustrating schematic configuration of a control system of an air purifying apparatus. A CPU 30 forms a central part of the control system, and is bus-interconnected with a ROM 31 that stores information such as a program, a RAM 32 that stores temporarily-generated information and a timer 33 for keeping time. The CPU 30 executes processing such as input, output and calculation in accordance with a control program stored in the ROM 31 in advance.

Further bus-interconnected with the CPU 30 are: an operating section 35 that receives operation such as turning on and turning off of the air purifying apparatus; a display section 36 including LCD that displays information such as contents of operation, an operating state or the like; and an air-blower driving circuit 37 that drives the motor 6 of the air blower 2.

The output interfaces 34 and 34 that are bus-interconnected with the CPU 30 are connected to control inputs PC1 and PC2 of ion generator driving circuits (driving circuits) 38 and 38, respectively. Each of one output ends of the ion generator driving circuits 38 and 38 is connected to the negative electrode of a direct-current power source E1 with the positive electrode thereof being connected to power inputs V1 and V2 of the ion generators 5, 5. The other ends of the ion generator driving circuits 38 and 38 are connected to ground inputs G1 and G2 of the ion generators 5 and 5, respectively.

With the configuration described above, every time the timer 33 clocks a given time, the CPU 30 alternately inverts ON and OFF of the control inputs PC1 and PC2 of the ion generator driving circuits 38, 38 via the output interfaces 34, 34. This allows the ion generator driving circuits 38, 38 to alternately connect/disconnect each of the ground inputs G1, G2 of the ion generators 5, 5 and the negative electrode of the direct-current power supply E1.

Figure 10:
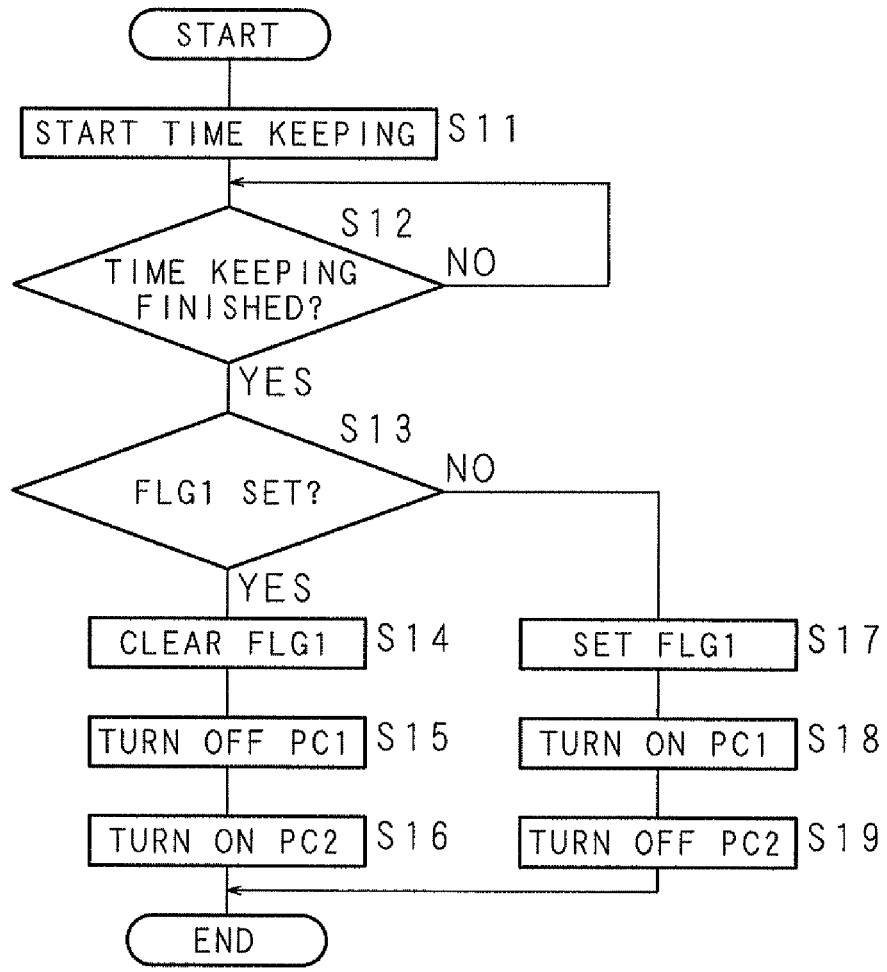
FIG. 10 is a flowchart illustrating a processing procedure of a CPU that drives an ion generator.

FIG. 10 is a flowchart illustrating a processing procedure of the CPU 30 that drives the ion generators 5, 5. The processing described below is executed as needed and is executed again every time the processing is terminated.

Note that the contents of FLG1 is stored in the RAM 32.

The CPU 30 makes the timer 33 start keeping time for one second (step S11). Subsequently, the CPU 30 determines whether or not the timer 33 has finished time keeping (step S12). If it is determined that the time keeping has not finished (NO at step S12), the CPU 30 waits until the timer 33 finishes time keeping. If it is determined that the time keeping has been finished (YES at step S12), the CPU 30 determines whether or not FLG1 is set (step S13).

If it is determined that FLG1 is set (YES at step S13), the CPU 30 clears FLG1 (step S14). Subsequently, the CPU 30 turns off the output of one output interface 34 to turn off the control input PC1 of the ion generator driving circuit 38 (step S15), while it turns on the output of another output interface 34 to turn on the control input PC2 of the ion generator driving circuit 38 (step S16), and terminates the processing.

If it is determined that FLG1 is not set at the step S13 (NO at step S13), the CPU 30 sets FLG1 (step S17). Subsequently, the CPU 30 turns on the output of one output interface 34 to turn on the control input PC1 of the ion generator driving circuit 38 (step S18), while it turns off the output of another output interface 34 to turn off the control input PC2 of the ion generator driving circuit 38 (step S19), and terminates the processing.

Figure 11:
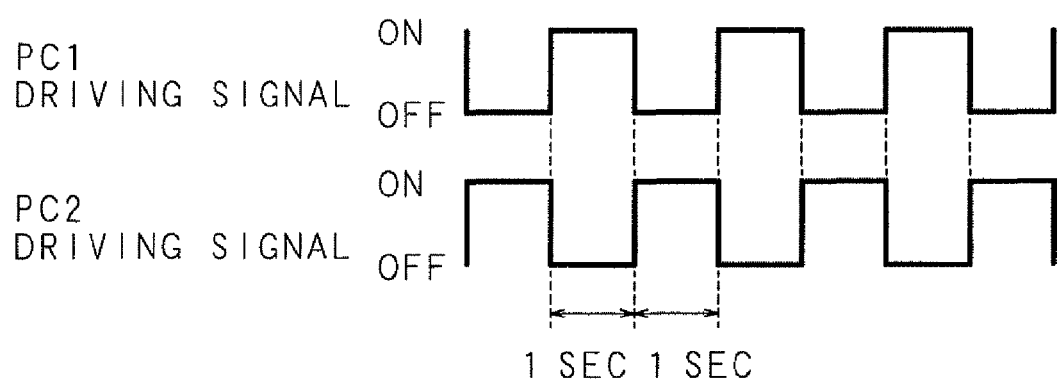
FIG. 11 is a timing chart of a driving signal input from each of output interfaces to a control input.

FIG. 11 is a timing chart of a driving signal input from each of the output interfaces 34, 34 to each of the control inputs PC1, PC2. Each driving signal alternately repeats ON for one second and OFF for one second with the duty of 50%. This allows the ion generator driving circuits 38, 38 to alternately connect and disconnect the power supply to the ion generators 5, 5 every other second. Accordingly, the ion generators 5, 5 are alternately driven every other second.

Figure 12:
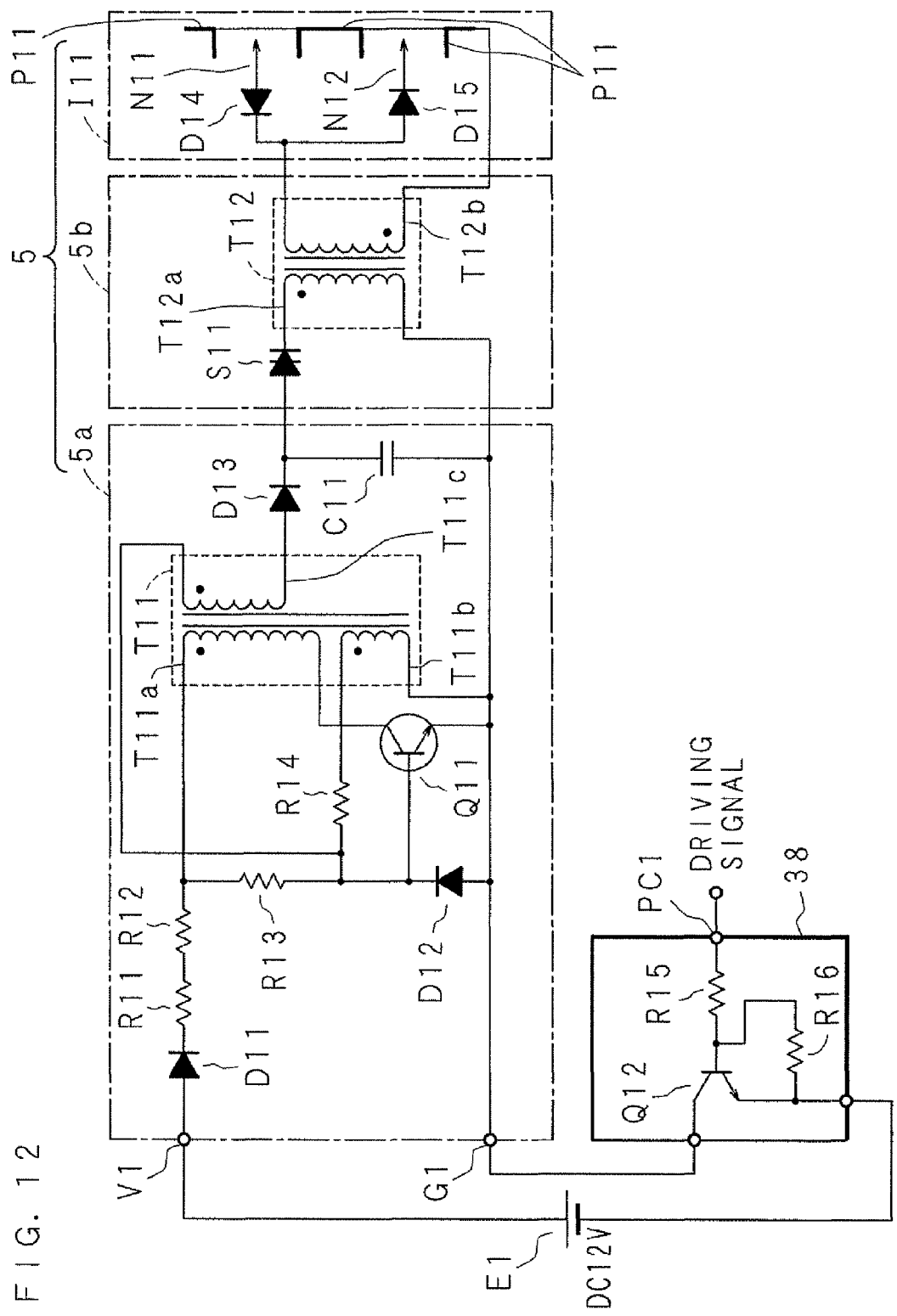
FIG. 12 is a circuit diagram illustrating an example of connection of an ion generator and an ion generator driving circuit.

FIG. 12 is a circuit diagram illustrating an example of connection of the ion generator 5 and the ion generator driving circuit 38. The ion generator 5 includes a first booster circuit 5a that raises the direct-current voltage applied between the power input V1 (or V2) and the ground input G1 (or G2), a second booster circuit 5b that further raises the voltage raised by the first booster circuit 5a, and an ion generating element I11 which is applied with the voltage raised by the second booster circuit 5b to generate ions.

The first booster circuit 5*a* includes: a series circuit having a diode D11 with the anode thereof connected to the power input V1 (or V2) and resistances R11, R12; a starting resistance R13 with one end connected to the resistance R12 side of the series circuit; and a booster transformer T11 with one end of a primary winding T11*a* connected to the connecting point between the resistance R12 and resistance R13.

The other end of the starting resistance R13 is connected to the cathode of the diode D12 with the anode thereof connected to the ground potential, the base of an emitter-grounded NPN transistor Q11 and one end of a secondary winding T11*c* of the booster transformer T11, while being connected to one end of a base winding T11*b* of the booster transformer T11 via a limiting resistance R14.

The other end of the primary winding T11*a* is connected to the collector of the NPN transistor Q11, while the other end of the base winding T11*b* is connected to the ground potential. The other end of the secondary winding T11*c* is connected to the anode of the diode D13, while the cathode of the diode D13 is connected to a charge condenser C11, with the other end thereof connected to the ground potential, and to the second booster circuit 5*b*.

The second booster circuit 5*b* includes a booster transformer T12 with one end of a primary winding T12*a* being connected to the first booster circuit 5*a* via a two-terminal thyristor S11. The other end of the primary winding T12*a* is connected to the ground potential, while both ends of the secondary winding T12*b* are connected to the ion generating element I11.

The ion generating element I11 includes: a diode D14 and a diode D15 with their respective cathode and anode connected to one end of the secondary winding T12*b* of the booster transformer T12; a negative-side needle electrode N11 and a positive-side needle electrode N12 connected, respectively, to the anode of the diode D14 and the cathode of the diode D15; and opposite electrodes P11 connected to the other end of the secondary winding T12*b*.

The ion generator driving circuit 38 includes: an NPN transistor Q12 with its collector and emitter connected, respectively, to the ground input G1 (or G2) and to the negative electrode of the direct-current power supply E1; a resistance R16 connected between the base and emitter of the NPN transistor Q12; and a resistance R15 connected between the base of the NPN transistor Q1 and the control input PC1 (or PC2).

In the configuration described above, when the driving signal shown in FIG. 11 is applied to the control input PC1 (or PC2), the NPN transistor Q12 is turned on, while DC12V of the direct-current power source E1 is applied between the power input V1 (or V2) and the ground input G1 (or G2). Here, base current flowing in via the diode D11, resistances R11, R12 and starting resistance R13 causes collector current to start flowing in the NPN transistor Q11, generating voltage at both ends of the primary winding T11*a* of the booster transformer T11. This generates voltage corresponding to the winding ratio of the primary winding T11*a* to the base winding T11*b* at both ends of the base winding T11*b*.

Since the base winding T11*b* of the booster transformer T11 has the same polarity as the primary winding T11*a*, the voltage generated at both ends of the base winding T11*b* functions to accelerate increase in collector current of the NPN transistor Q1 and to increase the voltage at both ends of the primary winding. Here, since the polarity of the secondary winding T11*c* is set such that the voltage of a direction in which the diode D13 does not become conductive is generated, no current flows through the secondary winding.

Subsequently, when the rate of increase in the collector current in the NPN transistor Q11 decreases, the voltage at both ends of the primary winding T11*a* begins to fall, lowering the voltage at both ends of the base winding T11*b* and thus reducing the base current and collector current. Hence, the voltage at both ends of the primary winding T11*a* further falls at an accelerated pace. Here, at both ends of the secondary winding T11*c*, voltage is generated in a direction in which the diode D13 becomes conductive, charging up the charge condenser C11.

When charging-up of the charge condenser C11 proceeds so that the terminal voltage reaches a break over voltage (105V in the present Embodiment) of the two-terminal thyristor S11, the two-terminal thyristor S11 begins to become conductive as in Zener diode. When the conducting current reaches the break over current (1 mA for example), the two-terminal thyristor S11 becomes almost in a short-circuit condition, discharging the electric charge stored in the charge condenser C11 to the ground potential through the primary winding T12*a* of the booster transformer T12*a*.

Here, a boosted impulse-like high voltage is generated at the secondary winding T12*b*. Accordingly, the ion generating element I11, which is applied with high voltage from the secondary winding T12*b* of the booster transformer T12 via the diodes D14 and D15, generates negative ions between the negative-side needle electrode N11 and the opposite electrode P11 as well as positive ions between the positive-side needle electrode N12 and the opposite electrode P11.

Figure 14:
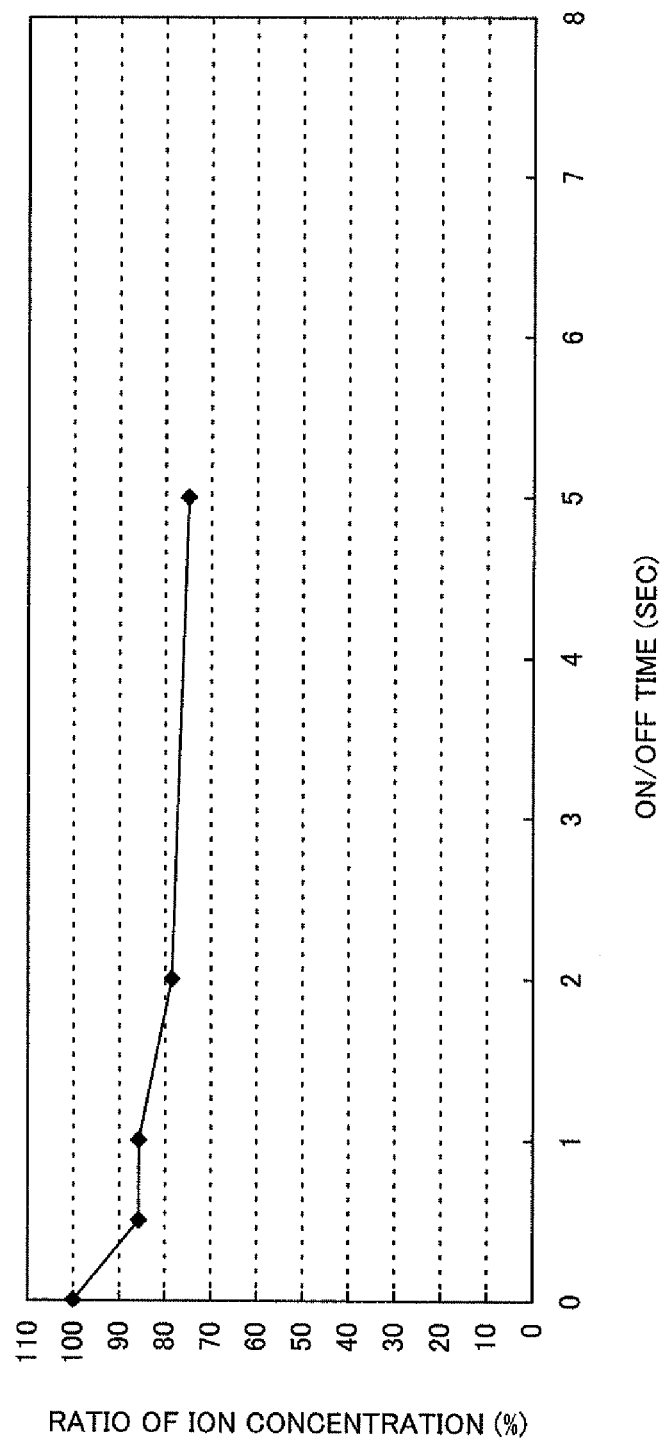
FIG. 14 is a graphic chart in which average values of the ratios of ion concentration shown in FIG. 13 are plotted.

FIG. 13 is a table illustrating an example of measurement in a room for ion concentration and ion balance when one ion generator 5 is constantly turned on (driven) and when it is alternately turned on and off, and for ratio of ion concentration obtained when the ion generator is constantly turned on to ion concentration obtained when it is alternately turned on and off. FIG. 14 is a graphic chart in which average values of the ratios of ion concentration shown in FIG. 13 are plotted. In FIG. 13, the ion concentration is indicated by the number of positive ions (ions/cm$^3$) and the number of negative ions (ions/cm$^3$) per unit volume, while the ion balance is indicated by the ratio of the ion concentration for positive ions to the ion concentration for negative ions. Moreover, in FIG. 14, the horizontal axis indicates time of on/off (second) whereas the vertical axis indicates the ratio of ion concentration (%).

In the measurement example shown in FIGS. 13 and 14, when the time of "on" and time of "off" are changed between 0.5 and 5 seconds with the duty for turning on/off the ion generator 5 maintained at 50%, the ratio of ion concentration is lowered from 85.7% to 75.0% compared to the case where the ion generator 5 is constantly turned on. The ratio of ion concentration obtained when the ion generator 5 is turned on/off for 0.5 seconds and 1 second corresponds to 85.7%, indicating only 14.3% decrease. In other words, the table shows that no large difference occurs in ion concentration when the ion generator 5 is intermittently driven with a period of one to two seconds, compared to the case where it is constantly driven.

Figure 16:
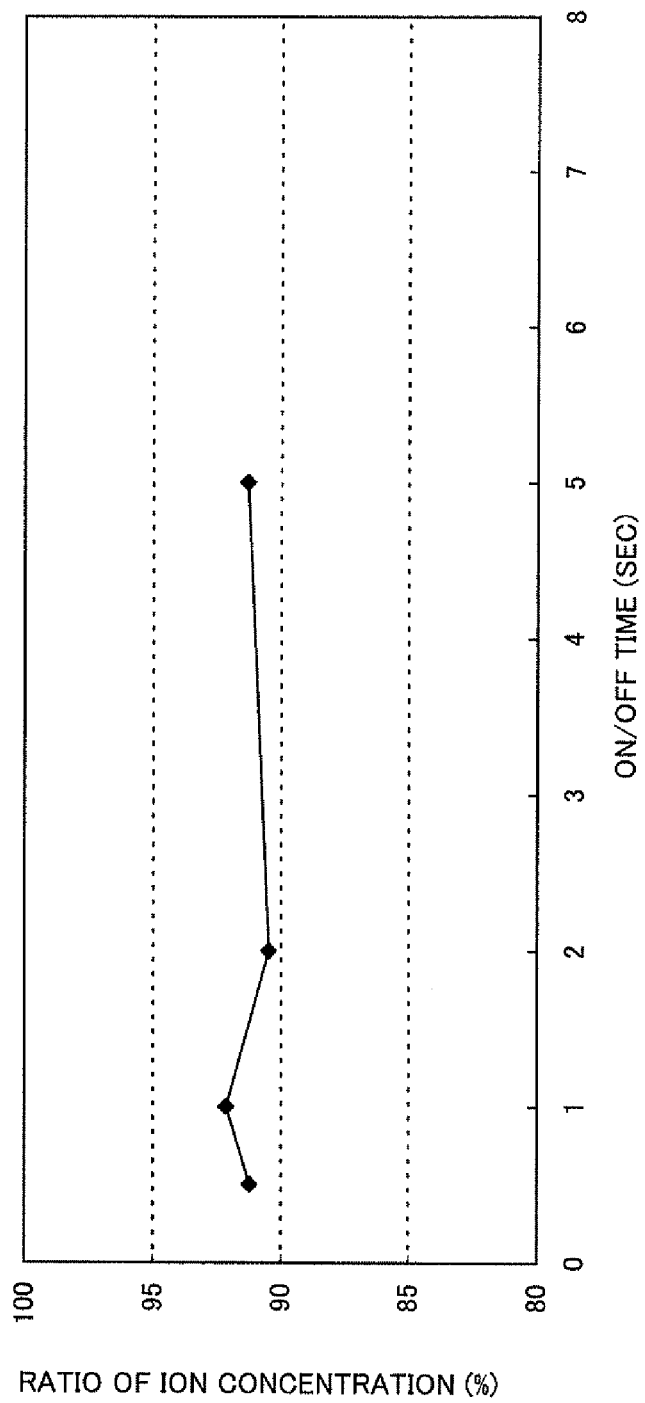
FIG. 16 is a graphic chart in which average values of the ratios of ion concentration shown in FIG. 15 are plotted.

FIG. 15 is a table illustrating an example of measurement in a room for ion concentration and ion balance when two ion generators 5 are constantly turned on and when they are alternately turned on and off, and for ratio of ion concentration obtained when the ion generators are constantly turned on to ion concentration obtained when they are alternately turned on and off. FIG. 16 is a graphic chart in which average values of the ratios of ion concentration shown in FIG. 15 are plotted. In FIG. 15, examples of measurement are also shown for ion concentration, ion balance and the ratio of ion concentration obtained when one ion generator 5 is constantly turned on. As for the units representing ion concentration and ion balance in FIG. 15, units similar to those in FIG. 13 are used. Moreover, in FIG. 16, the horizontal axis indicates time for on/off (seconds) whereas the vertical axis indicates the ratio of ion concentration (%).

In the measurement example shown in FIGS. 15 and 16, when the time for "on and "off" are changed between 0.5 to 5 seconds with the duty for turning on/off the ion generator 5 maintained at 50%, the ratio of ion concentration is lowered, in average value, from 92.2% to 90.5%, compared to when two ion generators 5 are constantly on. Among these, the ratio of ion concentration when the ion generators 5 are turned on/off for one second corresponds to 92.2% in average, indicating only 7.8% decrease. The ratio of ion concentration obtained when one ion generator 5 is constantly turned on is, on the other hand, 89.4%, indicating that higher ion concentration can be obtained by turning on/off two ion generators compared to the case where one ion generator is constantly turned on.

As described above, according to the present Embodiment, the ion generator driving circuit drives two ion generators in different phases on a periodic basis.

This prevents the ion generators from interfering with each other while lowering the energizing rate of the ion generators and thus extending operational lifetime of the ion generating apparatus. Hence, the operation lifetime can be extended without little decrease in the amount of ions dispersed in a space where ions are discharged, achieving a longer operating life of the ion generating apparatus.

Moreover, the ion generator arranged on the circular-arc guide wall of the casing is separated from the ion generator arranged on the front wall of the duct.

Accordingly, the probability that the ion generators interfere with each other causing decrease in the amount of generation of ions can be lowered.

Furthermore, the impeller of the air blower blows out the ions generated by two ion generators to the outside.

Accordingly, the ion generators can further be prevented from interfering with each other, while the generated ions can efficiently be guided to the outside.

Furthermore, the ion generator driving circuit alternately drives two ion generators with a period of two seconds, each for one second, at which the maximum amount of ions can be obtained.

Accordingly, compared to the case where two ion generators are continuously driven, the operational lifetime of the ion generating apparatus using the ion generators may be doubled without much decrease in the amount of generated ions.

Furthermore, the ions generated by the ion generators in the ion generating apparatus are included in the air purified by a filter.

Accordingly, the ion generating apparatus for which the operational life is extended without much decrease in the ions dispersed in a space where ions are discharged can be applied to an air purifying apparatus.

Though, in the present Embodiment, the ion generator is driven by repeating "on" for one second and "off" for one second with the duty of 50%, it is not limited thereto. The duty may be smaller than 50% to further extend the operational lifetime, or the ion generator can be driven with a period other than two seconds.

Moreover, the number of ion generators is not limited to two, but may be three or more. When, for example, three ion generators are provided, one more output interface 34 and one more ion generator driving circuit 38 as shown in FIG. 9 may be added. Furthermore, a PC3 driving signal may be added to the driving signals of each ion generator shown in FIG. 11, while the duty for each driving signal may be set as 33% such that "on" periods for the PC1 driving signal, PC2 driving signal and PC3 driving signal do not overlap with one another.

Embodiment 3

Figure 17:
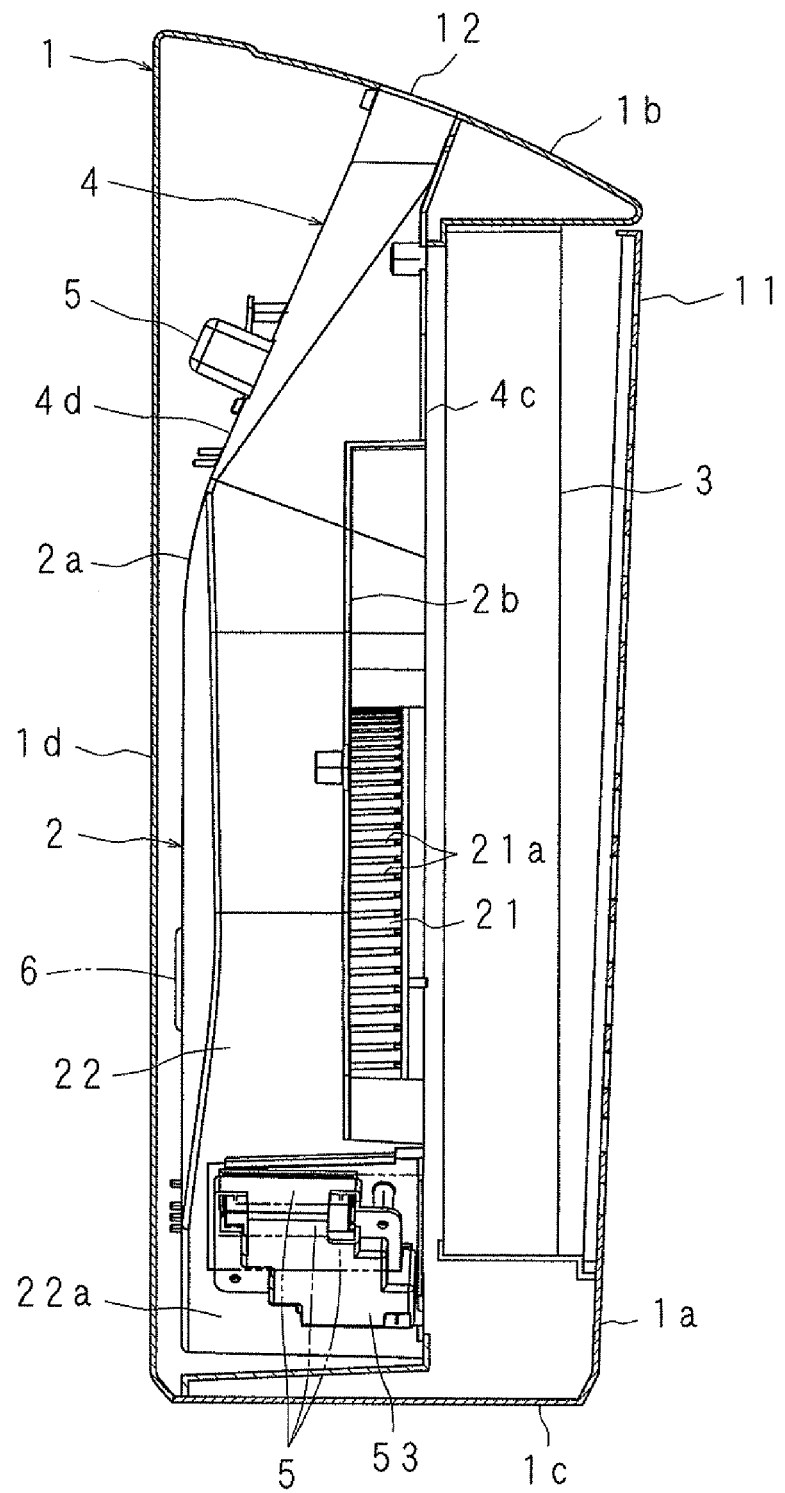
FIG. 17 is a vertical section side view illustrating the configuration of an air purifying apparatus according to an embodiment of the present invention.
Figure 18:
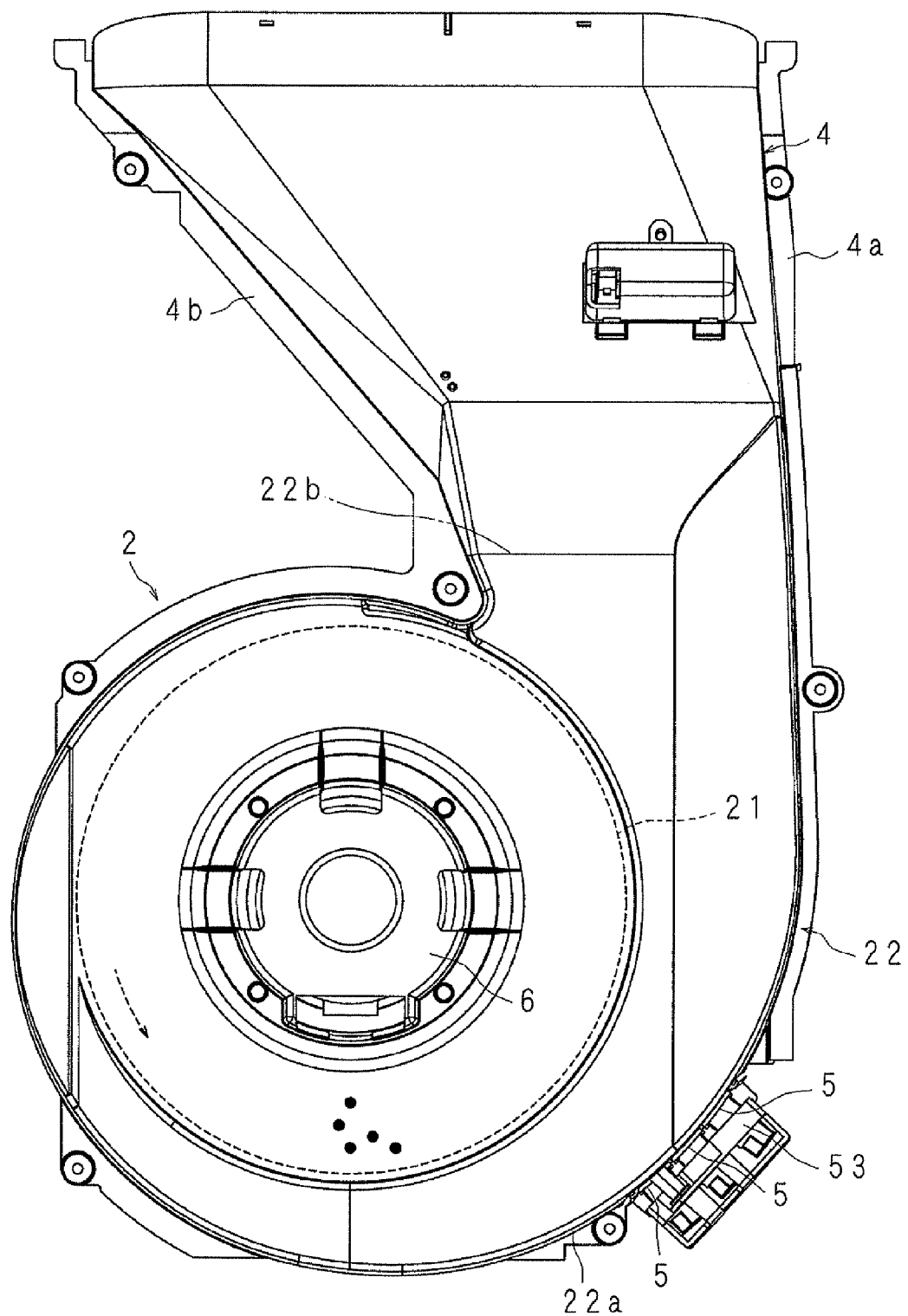
FIG. 18 is a front view illustrating the configuration of a main part.
Figure 19:
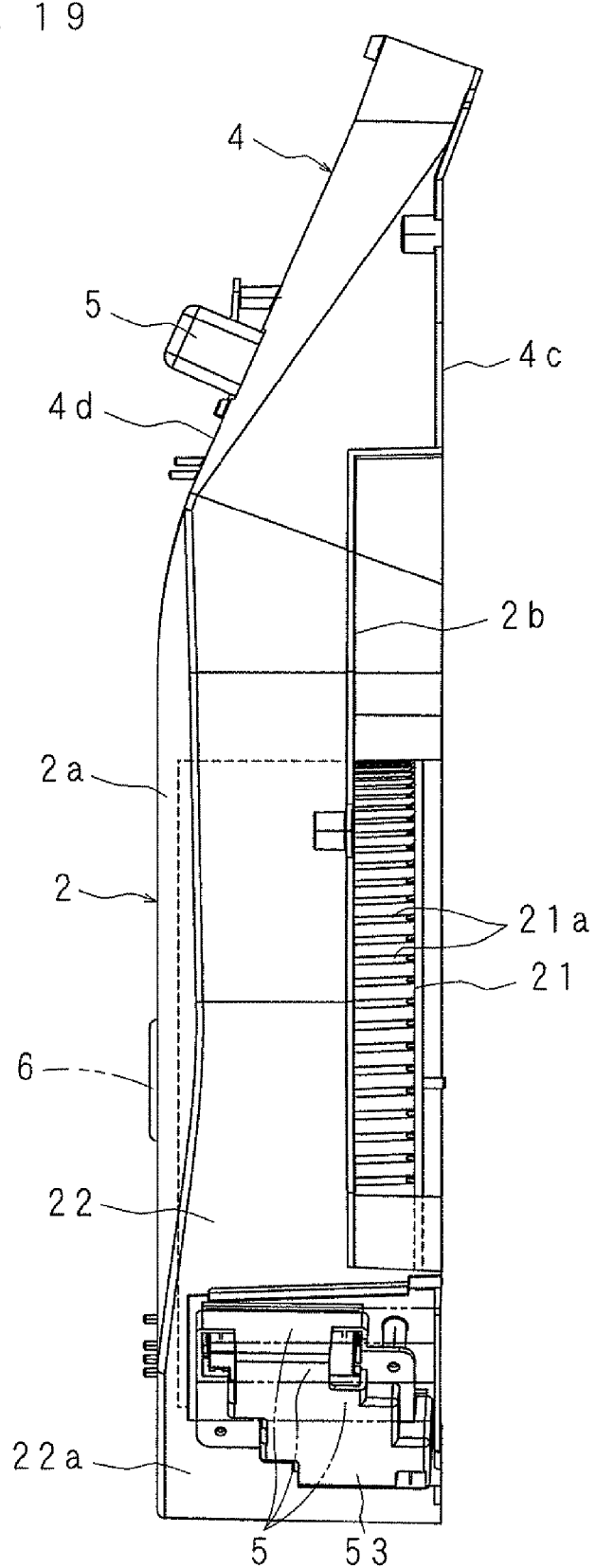
FIG. 19 is a side view illustrating the configuration of a main part.
Figure 20:
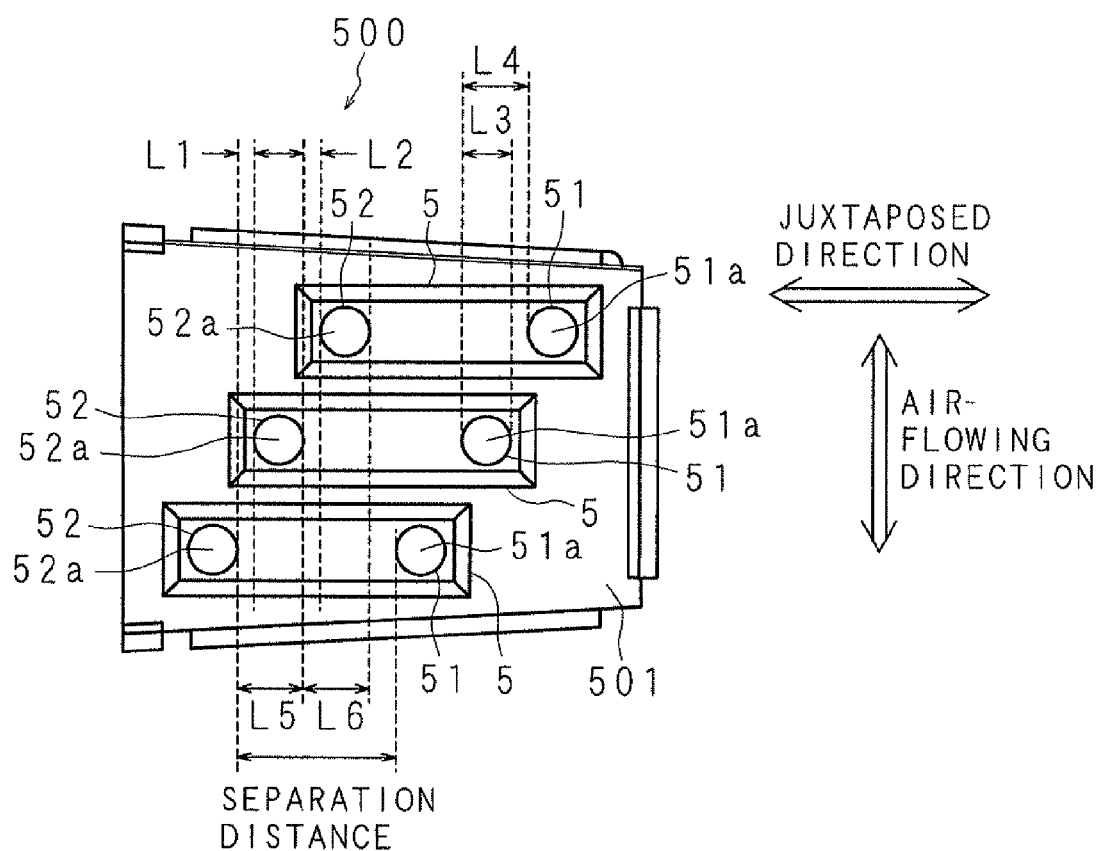
FIG. 20 is a front view illustrating an outer appearance of an ion generating apparatus.

Embodiments in which an ion generating apparatus according to the present invention is applied to an air purifying apparatus will be described below. FIG. 17 is a vertical section side view illustrating the configuration of an air purifying apparatus according to the present invention. FIG. 18 is a front view illustrating the configuration of a main part. FIG. 19 is a side view illustrating the configuration of a main part. FIG. 20 is a front view illustrating an outer appearance of an ion generating apparatus.

Reference numeral 1 in the drawings denotes a housing having a shape of an approximately rectangular parallelepiped. The housing 1 includes a suction port 11 on a back wall 1a for taking in the room air. Ahead the suction port 11, a filter (purifier) 3 is arranged for removing foreign materials from the air suctioned from the suction port 11 by the air blower 2 arranged at a lower part in the housing 1 and producing clean air. Above the air blower 2, a duct 4 is arranged as an air-flowing path for letting through the clean air toward the discharge port 12 located on a top wall 1b of the housing 1.

The housing 1 has a bottom wall 1c of a rectangular shape in planar view that continues into the lower side of the back wall 1. One side on the front side of the bottom wall 1c continues into the front wall 1d, while the other two sides continue into the side walls. The suction port 11 on the back wall 1a forms a rectangle with the longitudinal direction thereof being top and bottom, whereas the suction port 12 on the top wall 1b forms a rectangle with the longitudinal direction thereof being the both side walls.

The air blower 2 forms a cylindrical and centrifugal shape having an impeller 21 with its rotation shaft arranged back and forth, and a casing 22 in which the impeller 21 is housed to be rotatable. A motor 6 which drives the impeller 21 is attached to the front part of the casing 22.

The impeller 21 is a multi-blade impeller having a plurality of blades 21a with the side of its rotating center displaced in the rotating direction relative to the outer edge. In other words, it is a Sirocco impeller (Sirocco fan) having a circular-cylindrical shape. One end of the impeller 21 has a bearing board. The output shaft of the motor 6 is attached to a shaft hole opened at the center of the bearing board, which functions such that the air taken in from an opening at the other end to an air hole at the center is released from between the blades 21a on the outer circumference.

The casing 22 has a circular-arc guide wall 22a that guides the airflow generated by rotation of the impeller 21 in the rotating direction to increase the speed of the airflow, and a blowing port 22b opened upward from a part of the circular-arc guide wall 22a to one direction of the tangent line of the circular-arc guide wall 22a. The blowing port 22b forms a square-tubular shape that protrudes from a part of the circular-arc guide wall 22a in one direction of the tangent line of the circular-arc guide wall 22a. Moreover, the casing 22 forms the shape of a deep dish, including a casing body 2a having the circular-arc guide wall 22a and an opening for a blowing port 22b, and including a cover plate 2b on which the portion corresponding to the opening of the impeller 21 is opened and which closes the open side of the casing body 2a, the cover plate 2b being attached to the casing body 2a with a plurality of male screws.

The circular-arc guide wall 22a of the casing 22 has a penetration hole corresponding to an ion generating apparatus 500 as well as an attachment hole separately arranged from the penetration hole, the ion generating apparatus 500 being attached by a male screw which is screwed into the attachment hole.

The duct 4 forms a square-tubular shape with its lower end continuing into the blowing port 22b and its upper end being opened, and is integrally formed with the casing body 2a and the cover plate 2b. Moreover, the duct 4 includes: one side wall 4a arranged along one direction of the tangent line of the circular-arc guide wall 22a from one side of the blowing port 22b; another side wall 4b with a separation distance from the one side wall 4a gradually increasing from the other side of the blowing port 22b; a back wall 4c continuing into the one side wall 4a and another side wall 4b and vertically arranged; and a front wall 4d with a separation distance from the back wall 4c gradually decreases from the blowing port 22b. The duct 4 is configured to guide the clean air blown out from the blowing port 22b to form laminar flow along the one side wall 4a, back wall 4c and front wall 4d. Moreover, on the front wall 4d, a penetration hole corresponding to the ion generator 5 as well as an attachment hole which is separated from the penetration hole are opened. The ion generator 5 is attached by a male screw which is inserted into the attachment hole.

In the ion generator 5, two ion generating sections (positive and negative ion generating sections) 51 and 52 having, respectively, circular openings 51a and 52a that are separated from each other in a direction approximately vertically intersecting with the air-flowing direction of the clean air sent by the air blower 2 are juxtaposed with each other. Each of the ion generating sections 51 and 52 includes, at the inner-back side of each of the openings 51a and 52a, a discharge electrode of a peaked shape and an opposite electrode enclosing the discharge electrode. It is thus configured that one ion generating section 51 generates positive ions whereas another ion generating section 52 generates negative ions toward the side in which the respective openings 51a and 52a are directed.

The ion generating apparatus 500 includes three ion generators 5, 5 and 5 as well as a holder 501 that holds the ion generators 5, 5 and 5. The ion generating sections 51 and 52 in each of the ion generators 5, 5 and 5 face the casing 22 from the penetration hole. The side of the holder 501 to be attached to the casing 22 has a curved surface which curves in the air-flowing direction, the curved surface having the ion generators 5, 5 and 5 thereon. Moreover, the tangent line of the curved surface at positions where the ion generators 5, 5 and 5 are arranged is made to be approximately parallel with the respective openings 51a and 52a.

The ion generators 5, 5, 5 of the ion generating apparatus 500 are juxtaposed with and separated from each other in the air-flowing direction (arc direction of the circular-arc guide wall 22a). Adjacent ion generators 5 and 5 are biased in the direction approximately vertically intersecting with the air-flowing direction, i.e. the juxtaposed direction of the ion generating sections 51 and 52) by the bias amounts of L5 and L6 (see FIG. 20). The ion generating sections 51 and 52 of each of the ion generators 5, 5 and 5 are arranged such that they have the same polarity arrangement in the biasing direction and that they do not overlap with each other in the air-flowing direction. In other words, the bias amounts L5 and L6 of the adjacent ion generators 5 and 5 are set larger by a distance L1 and a distance L2, respectively, than the diameter of each of the openings 52a and 52a in the negative ion generating sections 52 and 52. This prevents airflow passing through along the ion generating sections 51 and 52 from overlapping with each other.

Moreover, the bias amount for each of the ion generators 5, 5 and 5 is made equal to or larger than the length of each of the openings 51a and 52a in the juxtaposed direction. In other words, the bias amount L4 for the ion generators 5 and 5 in FIG. 20 is, for example, set to be equal to or larger than an opening length L3 of the opening 51a in the positive ion generating section 51. This prevents airflow passing through along the openings 51a and 52a from overlapping with each other.

Furthermore, the total amount of bias for the ion generator 5 is set to be equal to or smaller than the separation distance between the ion generating sections 51 and 52. In other words, the sum of the bias amounts L5 and L6 for the adjacent ion generators 5, 5 and 5 is equal to or smaller than the separation distance between the positive and negative ion generating sections 51 and 52. This separates the airflow passing through along the ion generating sections 51, 51 and 51 from the airflow passing through along the ion generating sections 52, 52 and 52 to be on both sides of the juxtaposed direction.

The air purifying apparatus configured as described above is installed in the vicinity of a wall in a residential room such that the suction port 11 comes on the side of a wall. The air blower 2 is driven to rotate the impeller 21, which causes the air in the room to be suctioned into the housing 1 from the suction port 11 and generates an air-flowing path of wind between the suction port 11 and the discharge port 12. The filter 3 removes foreign materials such as dust from the suctioned air to produce clean air.

The clean air passed through the filter 3 is suctioned into the casing 22 of the air blower 2. Here, the clean air suctioned into the casing 22 becomes laminar flow by the circular-arc guide wall 22a around the impeller 21. The laminar flow is guided to the blowing port 22b along the circular-arc guide wall 22a and is blown from the blowing port 22b into the duct 4. The circular-arc guide wall 22a of the casing 22 in the air blower 2 is provided with the ion generating apparatus 500, which generates positive and negative ions in the clean air passing through along the circular-arc guide wall 22a.

The duct 4 is configured to guide the clean air as laminar flow along one side wall 4a, back wall 4c and front wall 4d, the ion generator 5 being arranged on the front wall 4d that guides the clean air to form laminar flow. Thus, in addition to the positive and negative ions generated in the clean air in the casing 22 of the air blower 2, the ion generator 5 arranged in the duct 4 further increases the amount of positive and negative ions. The positive and negative ions generated by the ion generating apparatus 500 and the ion generator 5 are discharged to the outside from the discharge port 12 together with the clean air sent by the air blower 2.

As described above, according to the present Embodiment, three ion generators each having positive and negative ion generating sections juxtaposed with each other are arranged on holders such that the ion generating sections have the same polarity arrangement in the juxtaposed direction. Moreover, the ion generators are biased in the juxtaposed direction such that the positive and negative ion generating sections do not overlap with each other. The ion generating apparatus is arranged in an air-flowing path such that the juxtaposed direction is approximately perpendicular to the direction of airflow passing through near the ion generating sections. This prevents ions generated by the ion generating sections from overlapping with each other.

Accordingly, mutual interference can be suppressed even when the ion generators are collectively arranged, alleviating decrease in ion generation efficiency.

Moreover, three ion generators are arranged in the direction intersecting with the juxtaposed direction of the ion generating sections, while the ion generating sections generate ions to one side in the direction vertically intersecting with the arrangement direction. Also, the ion generating apparatus is arranged in the air-flowing path such that the arrangement direction is approximately in parallel with the direction of airflow passing through near the ion generating sections.

Accordingly, even when the ion generators are arranged in a collective manner, the ions generated by each ion generating section can efficiently pass through together with the airflow.

Furthermore, the bias amount of the ion generators in the juxtaposed direction is set equal to or larger than the length of the opening in the juxtaposed direction. The ion generating apparatus is arranged in the air-flowing path such that the juxtaposed direction is approximately vertical to the direction of airflow passing through in the vicinity of each ion generating section. This prevents the ions generated by the ion generating sections via openings from overlapping with each other.

Hence, mutual interference can be suppressed even when the ion generators are arranged in a collective manner, alleviating decrease in ion generation efficiency.

Furthermore, the ion generating apparatus is biased in one direction, while the sum of biased amounts of the adjacent ion generators in the juxtaposed direction is set as equal to or smaller than the separation distance between the positive and negative ion generating sections. The ion generating apparatus is arranged in the air-flowing path such that the juxtaposed direction is approximately vertical to the direction of airflow passing through in the vicinity of each ion generating section. Accordingly, the ions generated by the positive ion generating section and negative ion generating section located separately on both sides in the juxtaposed direction do not overlap with each other.

Hence, mutual interference can be suppressed even when the ion generators are arranged in a collective manner, alleviating decrease in ion generation efficiency.

Furthermore, the ions generated by the ion generator in the ion generating apparatus can be included in the air purified by the filter.

Accordingly, an ion generating apparatus capable of suppressing mutual interference and alleviating decrease in ion generation efficiency even when ion generators are arranged in a collective manner can be applied to an air purifying apparatus.

Though the ion generating section has openings in the present Embodiment, it is not limited thereto. For example, an ion generating apparatus having a discharge electrode formed of a dielectric covered with a protective layer but not having an opening in the ion generating section may be employed.

Moreover, the number of ion generators arranged in the ion generating apparatus is not limited to three, but may be two, four or more.

What is claimed is:

1. An ion generating apparatus, comprising:
    a plurality of ion generators that generate ions;
    a CPU which is to be a center of a control system;
    a plurality of output interface devices which are connected to the CPU in parallel and output a driving signal to the plurality of ion generators; and
    a driving circuit that repeatedly drives the plurality of ion generators in turns in different phases at a duty of 50% or less to prevent the plurality of ion generators from interfering with each other,
    wherein a ratio of ion concentration obtained when the plurality of ion generators are alternately turned on and off at the duty is high compared to a case where one ion generator among the plurality of ion generators is constantly turned on.

2. The ion generating apparatus according to claim 1, wherein
    at least one of the plurality of ion generators is separated from another ion generator.

3. The ion generating apparatus according to claim 1, further comprising:
    an air-blowing fan that blows ions generated by the plurality of ion generators to an outside.

4. The ion generating apparatus according to claim 1, wherein the plurality of ion generators includes two of the ion generators, and wherein
    the driving circuit alternately drives the two ion generators.

5. An air purifying apparatus, comprising:
    an ion generating apparatus according to claim 1; and
    a purifier that purifies the air including ions generated by the ion generating apparatus.

6. The ion generating apparatus according to claim 4, wherein the two of the ion generators are alternatively driven for about one second at a time.

* * * * *